United States Patent
Dong

(10) Patent No.: US 8,377,865 B2
(45) Date of Patent: Feb. 19, 2013

(54) GROWTH HORMONE RELEASING PEPTIDES

(75) Inventor: Zheng Xin Dong, Holliston, MA (US)

(73) Assignee: IPSEN Pharma S.A.S., Boulogne (FR)

( * ) Notice: Subject to any disclaimer, the term of this patent is extended or adjusted under 35 U.S.C. 154(b) by 590 days.

(21) Appl. No.: 12/157,224

(22) Filed: Jun. 9, 2008

(65) Prior Publication Data

US 2008/0242619 A1 Oct. 2, 2008

Related U.S. Application Data

(63) Continuation of application No. 10/484,473, filed as application No. PCT/US03/24834 on Aug. 8, 2003, now Pat. No. 7,456,253.

(60) Provisional application No. 60/402,263, filed on Aug. 9, 2002.

(51) Int. Cl.
*A61K 38/00* (2006.01)
*A61K 51/00* (2006.01)

(52) U.S. Cl. ......... 514/1.1; 530/300; 530/326; 530/327; 530/333; 424/1.69

(58) Field of Classification Search .................. None
See application file for complete search history.

(56) References Cited

U.S. PATENT DOCUMENTS

| | | | |
|---|---|---|---|
| 5,798,337 | A | 8/1998 | Somers et al. |
| 5,804,563 | A | 9/1998 | Still et al. |
| 5,932,548 | A | 8/1999 | Deghenghi |
| 2002/0111461 | A1 | 8/2002 | Somers et al. |

FOREIGN PATENT DOCUMENTS

| | | |
|---|---|---|
| EP | 1 197 496 | 4/2002 |
| WO | WO 95/17423 | 6/1995 |
| WO | WO 96/10040 | 4/1996 |
| WO | WO 96/15148 | 5/1996 |
| WO | WO 97/00894 | 1/1997 |
| WO | PCT 00/09537 | 2/2000 |
| WO | WO 00/29011 | 5/2000 |
| WO | PCT 01/07475 | 2/2001 |
| WO | WO 2006/045314 | 5/2006 |

OTHER PUBLICATIONS

Arvat et al, "Ghrelin and synthetic GH secretagogues", Best Pract. Res. Clin. Endocrinol. Metab., 2002, 16:505-17.

Chen et al., "Analogs of the orally active growth hormone secretagogue L-162,752", Bioorganic & Med. Chem. Lett., 1996, 6:2163-69.

Guan et al., "Distribution of mRNA encoding the growth hormone secretagogue receptor in brain and peripheral tissues," Mol. Brain. Res., 1997, 48:23-29.

Howard et al., "A receptor in pituitary and hypothalamus that functions in growth hormone release," Science, 1996, 273:974-77.

Kaiya et al., "Bullfrog ghrelin is modified by n-octanoic acid at its third threonine residue," J. Biol. Chem., 2001, 276:40441-48.

Kojima et al., "Ghrelin is a growth-hormone-releasing acylated peptide from stomach," Nature, 1999, 402:656-60.

Korbonits et al., "Presence of ghrelin in normal and adenomatous human pituitary," Endocrine, 2001, 14:101-04.

McKee et al., "Cloning and characterization of two human G protein-coupled receptor genes (GPR38 and GPR39) related to the growth hormone secretagogue and neurotensin receptors," Genomics, 1997, 46:426-34.

Patchett et al., "Design and biological activities of L-163,191 (MK-0677): A potent, orally active growth hormone secretagogue," Proc. Nat. Acad. Sci. USA, 1995, 92:7001-05.

Pong et al., "Identification of a new G-protein-linked receptor for growth hormone secretagogues," Molecular Endocrinology, 1996, 10:57-61.

Smith et al., "A nonpeptidyl growth hormone secretagogue," Science, 1993, 260:1640-43.

McDowell, et al , "Growth hormone secretagogues: Characterization, efficacy, and minimal bioactive conformation", PNAS, 1995, 92:11165-69.

Torsello, et al, "Novel hexarelin analogs stimulate feeding in the rat through a mechanism not involving growth hormone release", Europ. Journ. Pharm., 1998, 360(2-3):123-9.

*Primary Examiner* — Maury Audet
(74) *Attorney, Agent, or Firm* — Tony K. Uhm; Pamela C. Ball

(57) ABSTRACT

Disclosed are peptide and peptidomimetic compounds generally according to formula (I), and pharmaceutically acceptable salts thereof, that are useful as GHRP analogs: $R^1$-$A^1$-$A^2$-$A^3$-$A^4$-$A^5$-$R^2$ (I) or a pharmaceutically acceptable salt thereof, wherein: $A^1$ is Aib, Apc or Inp; $A^2$ is D-Bal, D-Bip, D-Bpa, D-Dip, D-1Nal, D-2Nal, D-Ser(Bzl), or D-Trp; $A^3$ is D-Bal, D-Bip, D-Bpa, D-Dip, D-1Nal, D-2Nal, D-Ser(Bzl), or D-Trp; $A^4$ is 2Fua, Orn, 2Pal, 3Pal, 4Pal, Pff, Phe, Pim, Taz, 2Thi, 3Thi, Thr(Bzl); $A^5$ is Apc, Dab, Dap, Lys, Orn, or deleted; $R^1$ is hydrogen, $(C_{1-6})$alkyl, $(C_{5-14})$aryl, $(C_{1-6})$alkyl$(C_{5-14})$aryl, $(C_{3-8})$cycloakyl, or $(C_{2-10})$acyl; and $R^2$ is OH or $NH_2$; and pharmaceutical compositions and methods of use thereof.

12 Claims, No Drawings

GROWTH HORMONE RELEASING PEPTIDES

This application is a continuation application of U.S. Ser. No. 10/484,473, filed Feb. 4, 2005, now U.S. Pat. No. 7,456,253, which is a United States national filing under 35 U.S.C. §371 of international (PCT) application No. PCT/US2003/024834, filed Aug. 8, 2003, designating the United States, and claiming priority to U.S. provisional application No. 60/402,263, filed Aug. 9, 2002.

BACKGROUND OF THE INVENTION

The pulsatile release of growth hormone from the pituitary somatotrops is regulated by two hypothalamic neuropeptides: growth hormone-releasing hormone and somatostatin. Growth hormone-releasing hormone stimulates release of growth hormone, whereas, somatostatin inhibits secretion of growth hormone. (Frohman et al., *Endocr. Rev.* 1986, 7, 223-253, and Strobi et al., *Pharmacol. Rev.* 1994, 46, 1-34.)

Release of growth hormone from the pituitary somatotrops can also be controlled by growth hormone-releasing peptides (GHRP's). A hexapeptide, His-D-Trp-Ala-Trp-D-Phe-Lys-amide (GHRP-6), was found to release growth hormone from somatotrops in a dose-dependent manner in several species including man. (Bowers et al., *Endocrinology* 1984, 114, 1537-1545.) Subsequent chemical studies on GHRP-6 led to the identification of other potent growth hormone secretagogues such as GHRP-I, GHRP-2 and hexarelin (Cheng et al., *Endocrinology* 1989, 124, 2791-2798, Bowers, C. Y. Novel GH-Releasing Peptides. In: *Molecular and Clinical Advances in Pituitary Disorders*. Ed: Melmed, S.; Endocrine Research and Education, Inc., Los Angeles, Calif., USA 1993, 153-157, and Deghenghi et al. *Life Sci.* 1994, 54, 1321-1328):

GHRP-I Ala-His-D-(2')-Nal-Ala-Trp-D-Phe-Lys-NH$_2$;
GHRP-2 D-Ala-D-(2')-Nal-Ala-Trp-D-Nal-Lys-NH$_2$;
Hexarelin His-D-2-MeTrp-Ala-Trp-D-Phe-Lys-NH$_2$.

GHRP-I, GHRP-2, GHRP-6, and hexarelin are synthetic growth hormone secretagogues (GHS's). GHS's stimulate secretion of growth hormone by a mechanism different from that of growth hormone-releasing hormone. (Bowers et al. *Endocrinology* 1984, 114, 1537-1545, Cheng et al. *Endocrinology* 1989, 124, 2791-2798, Bowers, C. Y. Novel GH-Releasing Peptides. In: *Molecular and Clinical Advances in Pituitary Disorders*. Ed: Melmed, S.; Endocrine Research and Education, Inc., Los Angeles, Calif., USA 1993, 153-157, and Deghenghi et al., *Life Sci.* 1994, 54, 1321-1328.)

The low oral bioavailability (<1%) of the peptidyl growth hormone secretagogues stimulated search for non-peptide compounds mimicking action of GHRP-6 in the pituitary. Several benzolactams and spiroindanes have been reported to stimulate growth hormone release in various animal species and in man. (Smith et al. *Science* 1993, 260, 1640-1643, Patchett et al., *Proc. Natl. Acad. Sci. USA.* 1995, 92, 7001-7005, and Chen et al., *Bioorg. Mod. Chem. Lett.* 1996, 6, 2163-2169.) A specific example of a small spiroindane is MK-0677 (Patchett et al. *Proc. Natl. Acad. Sci. USA.* 1995, 92, 7001-7005):

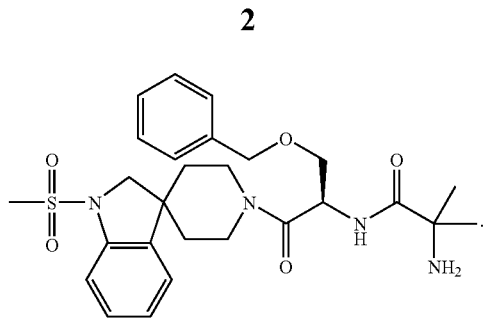

The actions of the above-mentioned GHS's (both peptide and non-peptide) appear to be mediated by a specific growth hormone secretagogue receptor (GHS receptor). (Howard et al., *Science* 1996, 273, 974-977, and Pong et al, *Molecular Endocrinology* 1996, 10, 57-61.) This receptor is present in the pituitary and hypothalamus of various mammalian species (GHSR1a) and is distinct from the growth hormone-releasing hormone (GHRH) receptor. The GHS receptor was also detected in the other areas of the central nervous system and in peripheral tissues, for instance adrenal and thyroid glands, heart, lung, kidney and skeletal muscles. (Chen et al, *Bioorg. Med. Chem. Lett.* 1996, 6, 2163-2169, Howard et al, *Science* 1996, 273, 974-977, Pong et al, *Molecular Endocrinology* 1996, 10, 57-61, Guan et al, *Mol. Brain Res.* 1997, 48, 23-29, and McKee et al., *Genomics* 1997, 46, 426-434.) A truncated version of GHSR1a has been reported. (Howard et al., *Science* 1996, 273, 974-977.)

The GHS receptor is a G-protein coupled-receptor. Effects of GHS receptor activation include depolarization and inhibition of potassium channels, an increase in intercellular concentrations of inositol triphosphate (IP3), and a transient increase in the concentrations of intracellular calcium. (Pong et al., *Molecular Endocrinology* 1996, 10, 57-61, Guan et al., *Mol. Brain Res.* 1997, 48, 23-29, and McKee et al., *Genomics* 1997, 46, 426-434.)

Ghrelin is a naturally occurring peptide which is believed to be an endogenous ligand for the GHS receptor. (Kojima et al., *Nature* 1999, 402, 656-660.) The native structures of ghrelins from several mammalian and non-mammalian species of animals are known. (Kaiya et al., *J. Biol. Chem.* 2001, 276, 40441-40448; International Patent Application PCT/JP00/04907 (WO 01/07475).) A core region present in ghrelin was found to provide for activity at the GHS receptor. The core region comprises the four N-terminal amino acids, where the serine at position 3 is normally modified with n-octanoic. However, in addition to acylation by n-octanoic acid native ghrelin also has been observed to be acylated with n-decanoic acid. (Kaiya et al., *J. Biol. Chem.* 2001, 276, 40441-40448.) Ghrelin analogs have a variety of different therapeutic uses as well as uses as research tools.

SUMMARY OF THE INVENTION

The present invention features peptidyl analogs active at the GHS receptor. The analogs of the invention can bind to the GHS receptor and, preferably, bring about signal transduction.

Thus, in a first aspect the present invention features a compound according to formula (I):

or a pharmaceutically acceptable salt thereof, wherein:
A$^1$ is Aib, Apc or Inp;
A$^2$ is D-Bal, D-Bip, D-Bpa, D-Dip, D-1Nal, D-2Nal, D-Ser(Bzl), or D-Trp;

A³ is D-Bal, D-Bip, D-Bpa, D-Dip, D-1Nal, D-2Nal, D-Ser(Bzl), or D-Trp;
A⁴ is 2Fua, Orn, 2Pal, 3Pal, 4Pal, Pff, Phe, Pim, Taz, 2Thi, 3Thi, Thr(Bzl);
A⁵ is Apc, Dab, Dap, Lys, Orn, or deleted;
R¹ is hydrogen, $(C_{1-6})$alkyl, $(C_{5-14})$aryl, $(C_{1-6})$alkyl$(C_{5-14})$aryl, $(C_{3-4})$cycloakyl, or $(C_{2-10})$acyl; and
R² is OH or $NH_2$;
provided that
when A⁵ is Dab, Dap, Lys, or Orn, then:
A² is D-Bip, D-Bpa, D-Dip or D-Bal; or
A³ is D-Bip, D-Bpa, D-Dip or D-Bal; or
A⁴ is 2Thi, 3Thi, Taz, 2Fua, 2Pal, 3Pal, 4Pal, Orn, Thr(Bzl), or Pff;
when A⁵ is deleted, then:
A³ is D-Bip, D-Bpa, or D-Dip; or
A⁴ is 2Fua, Pff, Taz, or Thr(Bzl); or
A¹ is Apc and—
A² is D-Bip, D-Bpa, D-Dip or D-Bal; or
A³ is D-Bip, D-Bpa, D-Dip or D-Bal; or
A⁴ is 2Thi, 3Thi, Orn, 2Pal, 3Pal, or 4Pal.
A preferred compound of formula (I), termed a Group 1 compound, is a compound according to formula (I) wherein:
A¹ is Aib, Apc or H-Inp;
A² is D-Bal, D-Bip, D-Bpa, D-Dip, D-1Nal, D-2Nal, D-Ser(Bzl), or D-Trp;
A³ is D-Bal, D-Bpa, D-Dip, D-1Nal, D-2Nal, or D-Trp;
A⁴ is Orn, 3Pal, 4Pal, Pff, Phe, Pim, Taz, 2Thi, or Thr(Bzl); and
A⁵ is Apc, Lys, or deleted;
or a pharmaceutically acceptable salt thereof.
A preferred Group 1 compound, termed a Group 1A compound, is a compound according to the formula:
A¹ is Apc or H-Inp;
A² is D-Bal, D-Bip, D-1Nal, or D-2Nal;
A³ is D-Bal, D-1Nal, D-2Nal, or D-Trp;
A⁴ is 3Pal, 4Pal, Pff, Phe, Pim, Taz, 2Thi, or Thr(Bzl); and
or a pharmaceutically acceptable salt thereof.
Another preferred compound of formula (I), termed a Group 2 compound, is a compound according to the formula:
H-Inp-D-1Nal-D-Trp-3Pal-Lys-NH₂;
H-Inp-D-2Nal-D-Trp-4Pal-Lys-NH₂;
H-Inp-D-2Nal-D-Trp-Orn-Lys-NH₂;
H-Inp-D-Bip-D-Trp-Phe-Lys-NH₂;
H-Inp-D-2Nal-D-Trp-Thr(Bzl)-Lys-NH₂;
H-Inp-D-2Nal-D-Trp-Pff-Lys-NH₂;
H-Inp-D-2Nal-D-Trp-2Thi-Lys-NH₂;
H-Inp-D-2Nal-D-Trp-Taz-Lys-NH₂;
H-Inp-D-Dip-D-Trp-Phe-Lys-NH₂;
H-Inp-D-Bpa-D-Trp-Phe-Lys-NH₂;
H-Inp-D-2Nal-D-Bpa-Phe-Lys-NH₂;
H-Inp-D-2Nal-D-Trp-3Pal-NH₂;
H-Inp-D-2Nal-D-Trp-4Pal-NH₂;
H-Inp-D-1Nal-D-Trp-3Pal-NH₂;
H-Inp-D-Bip-D-Trp-Phe-NH₂;
H-Inp-D-2Nal-D-Trp-Thr(Bzl)-NH₂;
H-Inp-D-2Nal-D-Trp-Pff-NH₂;
H-Inp-D-2Nal-D-Trp-2Thi-NH₂;
H-Inp-D-2Nal-D-Trp-Taz-NH₂;
H-Inp-D-Dip-D-Trp-Phe-NH₂;
H-Inp-D-2Nal-D-Dip-Phe-NH₂;
H-Inp-D-Bal-D-Trp-Phe-NH₂;
H-Inp-D-2Nal-D-Bal-Phe-NH₂;
H-Inp-D-2Nal-D-Trp-3Pal-Lys-NH₂;
H-Inp-D-Trp-D-2Nal(Ψ)-Pim;
H-Inp-D-Bal-D-Trp-2Thi-Lys-NH₂;
H-Inp-D-Bal-D-Trp-Phe-Lys-NH₂;
H-Inp-D-1Nal-D-Trp-2Thi-Lys-NH₂;
H-Inp-D-2Nal-D-Trp-Phe-Apc-NH₂;
H-Inp-D-1Nal-D-Trp-Phe-Apc-NH₂;
H-Inp-D-Bal-D-Trp-Phe-Apc-NH₂;
H-Apc-D-2Nal-D-Trp-Phe-Lys-NH₂;
H-Apc-D-1Nal-D-Trp-2Thi-Lys-NH₂;
H-Inp-D-1Nal-D-Trp-2Thi-NH₂;
H-Apc-D-1Nal-D-Trp-Phe-NH₂;
H-Inp-D-2Nal-D-Trp(Ψ)-Pim;
H-Inp-D-1Nal-D-Trp(Ψ)-Pim;
H-Inp-D-Bal-D-Trp(Ψ)-Pim;
H-Aib-D-Ser(Bzl)-D-Trp(Ψ)-Pim;
H-Inp-D-1Nal-D-Trp-Taz-Lys-NH₂;
H-Inp-D-Bal-D-Trp-Taz-Lys-NH₂;
H-Apc-D-1Nal-D-Trp-Taz-Lys-NH₂;
H-Apc-D-Bal-D-Trp-Taz-Lys-NH₂;
H-Apc-D-Bal-D-Trp-2Thi-Lys-NH₂;
H-Apc-D-Bal-D-Trp-Phe-Lys-NH₂;
H-Apc-D-1Nal-D-Trp-Phe-Apc-NH₂;
H-Apc-D-Bal-D-Trp-Phe-Apc-NH₂;
H-Apc-D-1Nal-D-1Nal-Phe-Apc-NH₂;
H-Apc-D-1Nal-D-2Nal-Phe-Apc-NH₂;
H-Apc-D-1Nal-D-1Nal-Phe-Lys-NH₂;
H-Apc-D-Bal-D-1Nal-Phe-Apc-NH₂;
H-Apc-D-Bal-D-2Nal-Phe-Apc-NH₂;
H-Apc-D-Bal-D-1Nal-Phe-Lys-NH₂;
H-Apc-D-Bal-D-2Nal-Phe-Lys-NH₂;
H-Apc-D-1Nal-D-Trp-2Thi-NH₂;
H-Apc-D-Bal-D-Trp-Phe-NH₂;
H-Apc-D-1Nal-D-Trp-Taz-NH₂;
H-Apc-D-Bal-D-Trp-2Thi-NH₂;
H-Apc-D-Bal-D-Trp-Taz-NH₂;
H-Apc-D-2Nal-D-Trp-2Thi-NH₂;
H-Apc-D-2Nal-D-Trp-Taz-NH₂;
H-Inp-D-1Nal-D-Trp-Taz-Apc-NH₂;
H-Inp-D-Bal-D-Trp-Taz-Apc-NH₂;
H-Apc-D-1Nal-D-Trp-Taz-Apc-NH₂;
H-Apc-D-Bal-D-Trp-Taz-Apc-NH₂;
H-Apc-D-1Nal-D-Trp-2Fua-Apc-NH₂;
H-Apc-D-1Nal-D-Trp-2Fua-Lys-NH₂;
H-Apc-D-1Nal-D-Trp-2Fua-NH₂;
H-Apc-D-1Nal-D-Trp-2Pal-NH₂;
H-Apc-D-1Nal-D-Trp-3Pal-NH₂;
H-Apc-D-1Nal-D-Trp-3Thi-Apc-NH₂;
H-Apc-D-1Nal-D-Trp-3Thi-Lys-NH₂;
H-Apc-D-1Nal-D-Trp-3Thi-NH₂;
H-Apc-D-1Nal-D-Trp-4Pal-NH₂;
H-Apc-D-1Nal-D-Trp-Pff-Apc-NH₂;
H-Apc-D-1Nal-D-Trp-Pff-Lys-NH₂;
H-Apc-D-1Nal-D-Trp-Pff-NH₂;
H-Apc-D-2Nal-D-Trp-2Fua-Apc-NH₂;
H-Apc-D-2Nal-D-Trp-2Fua-Lys-NH₂;
H-Apc-D-2Nal-D-Trp-2Fua-NH₂;
H-Apc-D-2Nal-D-Trp-2Pal-NH₂;
H-Apc-D-2Nal-D-Trp-2Thi-Apc-NH₂;
H-Apc-D-2Nal-D-Trp-2Thi-Lys-NH₂;
H-Apc-D-2Nal-D-Trp-3Pal-NH₂;
H-Apc-D-2Nal-D-Trp-3Thi-Apc-NH₂;
H-Apc-D-2Nal-D-Trp-3Thi-Lys-NH₂;
H-Apc-D-2Nal-D-Trp-3Thi-NH₂;
H-Apc-D-2Nal-D-Trp-4Pal-NH₂;
H-Apc-D-2Nal-D-Trp-Pff-Apc-NH₂;
H-Apc-D-2Nal-D-Trp-Pff-Lys-NH₂;
H-Apc-D-2Nal-D-Trp-Pff-NH₂;
H-Apc-D-2Nal-D-Trp-Taz-Apc-NH₂;
H-Apc-D-2Nal-D-Trp-Taz-Lys-NH₂;
H-Apc-D-Bal-D-Bal-2Fua-Apc-NH₂;

H-Apc-D-Bal-D-Bal-2Fua-Lys-NH$_2$;
H-Apc-D-Bal-D-Bal-2Fua-NH$_2$;
H-Apc-D-Bal-D-Bal-2Pal-NH$_2$;
H-Apc-D-Bal-D-Bal-2Thi-Apc-NH$_2$;
H-Apc-D-Bal-D-Bal-2Thi-Lys-NH$_2$;
H-Apc-D-Bal-D-Bal-2Thi-NH$_2$;
H-Apc-D-Bal-D-Bal-3Pal-NH$_2$;
H-Apc-D-Bal-D-Bal-3Thi-Apc-NH$_2$;
H-Apc-D-Bal-D-Bal-3Thi-Lys-NH$_2$;
H-Apc-D-Bal-D-Bal-3Thi-NH$_2$;
H-Apc-D-Bal-D-Bal-4Pal-NH$_2$;
H-Apc-D-Bal-D-Bal-Pff-Apc-NH$_2$;
H-Apc-D-Bal-D-Bal-Pff-Lys-NH$_2$;
H-Apc-D-Bal-D-Bal-Pff-NH$_2$;
H-Apc-D-Bal-D-Bal-Phe-Apc-NH$_2$;
H-Apc-D-Bal-D-Bal-Phe-Lys-NH$_2$;
H-Apc-D-Bal-D-Bal-Phe-NH$_2$;
H-Apc-D-Bal-D-Bal-Taz-Apc-NH$_2$;
H-Apc-D-Bal-D-Bal-Taz-Lys-NH$_2$;
H-Apc-D-Bal-D-Bal-Taz-NH$_2$;
H-Apc-D-Bal-D-Trp-2Fua-Apc-NH$_2$;
H-Apc-D-Bal-D-Trp-2Fua-Lys-NH$_2$;
H-Apc-D-Bal-D-Trp-2Fua-NH$_2$;
H-Apc-D-Bal-D-Trp-2Pal-NH$_2$;
H-Apc-D-Bal-D-Trp-3Pal-NH$_2$;
H-Apc-D-Bal-D-Trp-3Thi-Apc-NH$_2$;
H-Apc-D-Bal-D-Trp-3Thi-Lys-NH$_2$;
H-Apc-D-Bal-D-Trp-3Thi-NH$_2$;
H-Apc-D-Bal-D-Trp-4Pal-NH$_2$;
H-Apc-D-Bal-D-Trp-Pff-Apc-NH$_2$;
H-Apc-D-Bal-D-Trp-Pff-Lys-NH$_2$;
H-Apc-D-Bal-D-Trp-Pff-NH$_2$;
H-Inp-D-1Nal-D-Bal-2Fua-Lys-NH$_2$;
H-Inp-D-1Nal-D-Bal-2Fua-NH$_2$;
H-Inp-D-1Nal-D-Bal-2Thi-Lys-NH$_2$;
H-Inp-D-1Nal-D-Bal-3Thi-Lys-NH$_2$;
H-Inp-D-1Nal-D-Bal-Pff-Lys-NH$_2$;
H-Inp-D-1Nal-D-Bal-Pff-NH$_2$;
H-Inp-D-1Nal-D-Bal-Phe-Lys-NH$_2$;
H-Inp-D-1Nal-D-Bal-Taz-Lys-NH$_2$;
H-Inp-D-1Nal-D-Bal-Taz-NH$_2$;
H-Inp-D-1Nal-D-Trp-2Fua-Apc-NH$_2$;
H-Inp-D-1Nal-D-Trp-2Fua-Lys-NH$_2$;
H-Inp-D-1Nal-D-Trp-2Fua-NH$_2$;
H-Inp-D-1Nal-D-Trp-3Thi-Apc-NH$_2$;
H-Inp-D-1Nal-D-Trp-3Thi-Lys-NH$_2$;
H-Inp-D-1Nal-D-Trp-Pff-Apc-NH$_2$;
H-Inp-D-1Nal-D-Trp-Pff-Lys-NH$_2$;
H-Inp-D-1Nal-D-Trp-Pff-NH$_2$;
H-Inp-D-1Nal-D-Trp-Taz-NH$_2$;
H-Inp-D-2Nal-D-Trp-2Fua-Apc-NH$_2$;
H-Inp-D-2Nal-D-Trp-2Fua-NH$_2$;
H-Inp-D-2Nal-D-Trp-2Thi-Apc-NH$_2$;
H-Inp-D-2Nal-D-Trp-3Thi-Apc-NH$_2$;
H-Inp-D-2Nal-D-Trp-3Thi-Lys-NH$_2$;
H-Inp-D-2Nal-D-Trp-3Thi-NH$_2$;
H-Inp-D-2Nal-D-Trp-Pff-Apc-NH$_2$;
H-Inp-D-2Nal-D-Trp-Pff-NH$_2$;
H-Inp-D-2Nal-D-Trp-Taz-Apc-NH$_2$;
H-Inp-D-2Nal-D-Trp-Taz-NH$_2$;
H-Inp-D-Bal-D-Bal-2Fua-Lys-NH$_2$;
H-Inp-D-Bal-D-Bal-2Fua-NH$_2$;
H-Inp-D-Bal-D-Bal-2Thi-Lys-NH$_2$;
H-Inp-D-Bal-D-Bal-3Thi-Lys-NH$_2$;
H-Inp-D-Bal-D-Bal-Pff-Lys-NH$_2$;
H-Inp-D-Bal-D-Bal-Pff-NH$_2$;
H-Inp-D-Bal-D-Bal-Phe-Lys-NH$_2$;
H-Inp-D-Bal-D-Bal-Taz-Lys-NH$_2$;
H-Inp-D-Bal-D-Bal-Taz-NH$_2$;
H-Inp-D-Bal-D-Trp-2Fua-Apc-NH$_2$;
H-Inp-D-Bal-D-Trp-2Fua-Lys-NH$_2$;
H-Inp-D-Bal-D-Trp-2Fua-NH$_2$;
H-Inp-D-Bal-D-Trp-3Thi-Apc-NH$_2$;
H-Inp-D-Bal-D-Trp-3Thi-Lys-NH$_2$;
H-Inp-D-Bal-D-Trp-Pff-Apc-NH$_2$;
H-Inp-D-Bal-D-Trp-Pff-Lys-NH$_2$;
H-Inp-D-Bal-D-Trp-Pff-NH$_2$;
H-Inp-D-Bal-D-Trp-Taz-NH$_2$;
H-Inp-D-Bip-D-Bal-2Fua-Lys-NH$_2$;
H-Inp-D-Bip-D-Bal-2Fua-NH$_2$;
H-Inp-D-Bip-D-Bal-2Thi-Lys-NH$_2$;
H-Inp-D-Bip-D-Bal-3Thi-Lys-NH$_2$;
H-Inp-D-Bip-D-Bal-Pff-Lys-NH$_2$;
H-Inp-D-Bip-D-Bal-Pff-NH$_2$; or
H-Inp-D-Bip-D-Bal-Taz-Lys-NH$_2$;
H-Inp-D-Bip-D-Bal-Taz-NH$_2$;
H-Inp-D-Bip-D-Trp-2Fua-Lys-NH$_2$;
H-Inp-D-Bip-D-Trp-2Fua-NH$_2$;
H-Inp-D-Bip-D-Trp-2Thi-Lys-NH$_2$;
H-Inp-D-Bip-D-Trp-3Thi-Lys-NH$_2$;
H-Inp-D-Bip-D-Trp-Pff-Lys-NH$_2$;
H-Inp-D-Bip-D-Trp-Pff-NH$_2$;
H-Inp-D-Bip-D-Trp-Taz-Lys-NH$_2$; or
H-Inp-D-Bip-D-Trp-Taz-NH$_2$;
or a pharmaceutically acceptable salt thereof.

A preferred Group 2 compound, termed a Group 2A compound, is a compound according to the formula:
H-Inp-D-1Nal-D-Trp-3Pal-Lys-NH$_2$;
H-Inp-D-2Nal-D-Trp-4Pal-Lys-NH$_2$;
H-Inp-D-2Nal-D-Trp-Orn-Lys-NH$_2$;
H-Inp-D-Bip-D-Trp-Phe-Lys-NH$_2$;
H-Inp-D-2Nal-D-Trp-Thr(Bzl)-Lys-NH$_2$;
H-Inp-D-2Nal-D-Trp-Pff-Lys-NH$_2$;
H-Inp-D-2Nal-D-Trp-2Thi-Lys-NH$_2$;
H-Inp-D-2Nal-D-Trp-Taz-Lys-NH$_2$;
H-Inp-D-Dip-D-Trp-Phe-Lys-NH$_2$;
H-Inp-D-Bpa-D-Trp-Phe-Lys-NH$_2$;
H-Inp-D-2Nal-D-Bpa-Phe-Lys-NH$_2$;
H-Inp-D-2Nal-D-Trp-Thr(Bzl)-NH$_2$;
H-Inp-D-2Nal-D-Trp-Pff-NH$_2$;
H-Inp-D-2Nal-D-Trp-Taz-NH$_2$;
H-Inp-D-2Nal-D-Dip-Phe-NH$_2$;
H-Inp-D-2Nal-D-Trp-3Pal-Lys-NH$_2$;
H-Inp-D-Trp-D-2Nal(Ψ)-Pim;
H-Inp-D-Bal-D-Trp-2Thi-Lys-NH$_2$;
H-Inp-D-Bal-D-Trp-Phe-Lys-NH$_2$;
H-Inp-D-1Nal-D-Trp-2Thi-Lys-NH$_2$;
H-Inp-D-2Nal-D-Trp-Phe-Apc-NH$_2$;
H-Inp-D-1Nal-D-Trp-Phe-Apc-NH$_2$;
H-Inp-D-Bal-D-Trp-Phe-Apc-NH$_2$;
H-Apc-D-2Nal-D-Trp-Phe-Lys-NH$_2$;
H-Apc-D-1Nal-D-Trp-2Thi-Lys-NH$_2$;
H-Inp-D-2Nal-D-Trp(Ψ)-Pim;
H-Inp-D-1Nal-D-Trp(Ψ)-Pim;
H-Inp-D-Bal-D-Trp(Ψ)-Pim;
H-Aib-D-Ser(Bzl)-D-Trp(Ψ)-Pim;
H-Inp-D-1Nal-D-Trp-Taz-Lys-NH$_2$;
H-Inp-D-Bal-D-Trp-Taz-Lys-NH$_2$;
H-Apc-D-1Nal-D-Trp-Taz-Lys-NH$_2$;
H-Apc-D-Bal-D-Trp-Taz-Lys-NH$_2$;
H-Apc-D-Bal-D-Trp-2Thi-Lys-NH$_2$;
H-Apc-D-Bal-D-Trp-Phe-Lys-NH$_2$;
H-Apc-D-1Nal-D-Trp-Phe-Apc-NH$_2$;
H-Apc-D-Bal-D-Trp-Phe-Apc-NH$_2$;

H-Apc-D-1Nal-D-1Nal-Phe-Apc-NH₂;
H-Apc-D-1Nal-D-2Nal-Phe-Apc-NH₂;
H-Apc-D-1Nal-D-1Nal-Phe-Lys-NH₂;
H-Apc-D-Bal-D-1Nal-Phe-Apc-NH₂;
H-Apc-D-Bal-D-2Nal-Phe-Apc-NH₂;
H-Apc-D-Bal-D-1Nal-Phe-Lys-NH₂;
H-Apc-D-Bal-D-2Nal-Phe-Lys-NH₂;
H-Apc-D-1Nal-D-Trp-2Thi-NH₂;
H-Apc-D-Bal-D-Trp-Phe-NH₂;
H-Apc-D-1Nal-D-Trp-Taz-NH₂;
H-Apc-D-Bal-D-Trp-2Thi-NH₂;
H-Apc-D-Bal-D-Trp-Taz-NH₂;
H-Apc-D-2Nal-D-Trp-2Thi-NH₂;
H-Apc-D-2Nal-D-Trp-Taz-NH₂;
H-Inp-D-1Nal-D-Trp-Taz-Apc-NH₂;
H-Inp-D-Bal-D-Trp-Taz-Apc-NH₂;
H-Apc-D-1Nal-D-Trp-Taz-Apc-NH₂;
H-Apc-D-Bal-D-Trp-Taz-Apc-NH₂;
H-Inp-D-2Nal-D-Trp-3Thi-Lys-NH₂;
H-Inp-D-Bal-D-Trp-3Thi-Lys-NH₂;
H-Inp-D-Bal-D-Trp-2Fua-Lys-NH₂;
H-Inp-D-Bal-D-Trp-Pff-Lys-NH₂;
H-Inp-D-Bal-D-Trp-3Thi-Apc-NH₂;
H-Inp-D-Bal-D-Trp-2Fua-Apc-NH₂;
H-Inp-D-Bal-D-Trp-Pff-Apc-NH₂;
H-Apc-D-Bal-D-Trp-3Thi-Lys-NH₂;
H-Apc-D-Bal-D-Trp-2Fua-Lys-NH₂;
H-Apc-D-Bal-D-Trp-Pff-Lys-NH₂;
H-Inp-D-Bal-D-Bal-Phe-Lys-NH₂;
H-Inp-D-Bal-D-Bal-2Thi-Lys-NH₂;
H-Inp-D-Bal-D-Bal-3Thi-Lys-NH₂;
H-Inp-D-Bal-D-Bal-Taz-Lys-NH₂;
H-Inp-D-Bal-D-Bal-2Fua-Lys-NH₂;
H-Inp-D-Bal-D-Bal-Pff-Lys-NH₂;
H-Apc-D-Bal-D-Bal-Phe-Lys-NH₂;
H-Apc-D-Bal-D-Bal-2Thi-Lys-NH₂;
H-Apc-D-Bal-D-Bal-3Thi-Lys-NH₂;
H-Apc-D-Bal-D-Bal-Taz-Lys-NH₂;
H-Apc-D-Bal-D-Bal-2Fua-Lys-NH₂;
H-Apc-D-Bal-D-Bal-Pff-Lys-NH₂;
H-Inp-D-1Nal-D-Trp-3Thi-Lys-NH₂;
H-Inp-D-1Nal-D-Trp-2Fua-Lys-NH₂;
H-Inp-D-1Nal-D-Trp-Pff-Lys-NH₂;
H-Inp-D-1Nal-D-Bal-Phe-Lys-NH₂;
H-Inp-D-1Nal-D-Bal-2Thi-Lys-NH₂;
H-Inp-D-1Nal-D-Bal-3Thi-Lys-NH₂;
H-Inp-D-1Nal-D-Bal-Taz-Lys-NH₂;
H-Inp-D-1Nal-D-Bal-2Fua-Lys-NH₂;
H-Inp-D-1Nal-D-Bal-Pff-Lys-NH₂;
H-Inp-D-2Nal-D-Trp-2Thi-Apc-NH₂;
H-Inp-D-2Nal-D-Trp-3Thi-Apc-NH₂;
H-Inp-D-2Nal-D-Trp-Taz-Apc-NH₂;
H-Inp-D-2Nal-D-Trp-2Fua-Apc-NH₂;
H-Inp-D-2Nal-D-Trp-Pff-Apc-NH₂;
H-Inp-D-1Nal-D-Trp-3Thi-Apc-NH₂;
H-Inp-D-1Nal-D-Trp-2Fua-Apc-NH₂;
H-Inp-D-1Nal-D-Trp-Pff-Apc-NH₂;
H-Apc-D-1Nal-D-Trp-3Thi-Lys-NH₂;
H-Apc-D-1Nal-D-Trp-2Fua-Lys-NH₂;
H-Apc-D-1Nal-D-Trp-Pff-Lys-NH₂;
H-Apc-D-2Nal-D-Trp-2Thi-Lys-NH₂;
H-Apc-D-2Nal-D-Trp-3Thi-Lys-NH₂;
H-Apc-D-2Nal-D-Trp-Taz-Lys-NH₂;
H-Apc-D-2Nal-D-Trp-2Fua-Lys-NH₂;
H-Apc-D-2Nal-D-Trp-Pff-Lys-NH₂;
H-Inp-D-Bip-D-Trp-2Thi-Lys-NH₂;
H-Inp-D-Bip-D-Trp-3Thi-Lys-NH₂;
H-Inp-D-Bip-D-Trp-Taz-Lys-NH₂;
H-Inp-D-Bip-D-Trp-2Fua-Lys-NH₂;
H-Inp-D-Bip-D-Trp-Pff-Lys-NH₂;
H-Inp-D-Bip-D-Bal-2Thi-Lys-NH₂;
H-Inp-D-Bip-D-Bal-3Thi-Lys-NH₂;
H-Inp-D-Bip-D-Bal-Taz-Lys-NH₂;
H-Inp-D-Bip-D-Bal-2Fua-Lys-NH₂;
H-Inp-D-Bip-D-Bal-Pff-Lys-NH₂;
H-Apc-D-Bal-D-Trp-3Thi-Apc-NH₂;
H-Apc-D-Bal-D-Trp-2Fua-Apc-NH₂;
H-Apc-D-Bal-D-Trp-Pff-Apc-NH₂;
H-Apc-D-Bal-D-Bal-Phe-Apc-NH₂;
H-Apc-D-Bal-D-Bal-2Thi-Apc-NH₂;
H-Apc-D-Bal-D-Bal-3Thi-Apc-NH₂;
H-Apc-D-Bal-D-Bal-Taz-Apc-NH₂;
H-Apc-D-Bal-D-Bal-2Fua-Apc-NH₂;
H-Apc-D-Bal-D-Bal-Pff-Apc-NH₂;
H-Apc-D-1Nal-D-Trp-3Thi-Apc-NH₂;
H-Apc-D-1Nal-D-Trp-2Fua-Apc-NH₂;
H-Apc-D-1Nal-D-Trp-Pff-Apc-NH₂;
H-Apc-D-2Nal-D-Trp-2Thi-Apc-NH₂;
H-Apc-D-2Nal-D-Trp-3Thi-Apc-NH₂;
H-Apc-D-2Nal-D-Trp-Taz-Apc-NH₂;
H-Apc-D-2Nal-D-Trp-2Fua-Apc-NH₂;
H-Apc-D-2Nal-D-Trp-Pff-Apc-NH₂;
H-Inp-D-Bal-D-Trp-Taz-NH₂;
H-Inp-D-Bal-D-Trp-2Fua-NH₂;
H-Inp-D-Bal-D-Trp-Pff-NH₂;
H-Apc-D-Bal-D-Trp-3Thi-NH₂;
H-Apc-D-Bal-D-Trp-2Fua-NH₂;
H-Apc-D-Bal-D-Trp-Pff-NH₂;
H-Apc-D-Bal-D-Trp-4Pal-NH₂;
H-Apc-D-Bal-D-Trp-3Pal-NH₂;
H-Apc-D-Bal-D-Trp-2Pal-NH₂;
H-Inp-D-Bal-D-Bal-Taz-NH₂;
H-Inp-D-Bal-D-Bal-2Fua-NH₂;
H-Inp-D-Bal-D-Bal-Pff-NH₂;
H-Apc-D-Bal-D-Bal-Phe-NH₂;
H-Apc-D-Bal-D-Bal-2Thi-NH₂;
H-Apc-D-Bal-D-Bal-3Thi-NH₂;
H-Apc-D-Bal-D-Bal-Taz-NH₂;
H-Apc-D-Bal-D-Bal-2Fua-NH₂;
H-Apc-D-Bal-D-Bal-Pff-NH₂;
H-Apc-D-Bal-D-Bal-4 Pal-NH₂;
H-Apc-D-Bal-D-Bal-3 Pal-NH₂;
H-Apc-D-Bal-D-Bal-2 Pal-NH₂;
H-Inp-D-1Nal-D-Trp-Taz-NH₂;
H-Inp-D-1Nal-D-Trp-2Fua-NH₂;
H-Inp-D-1Nal-D-Trp-Pff-NH₂;
H-Inp-D-1Nal-D-Bal-Taz-NH₂;
H-Inp-D-1Nal-D-Bal-2Fua-NH₂;
H-Inp-D-1Nal-D-Bal-Pff-NH₂;
H-Inp-D-2Nal-D-Trp-Taz-NH₂;
H-Inp-D-2Nal-D-Trp-2Fua-NH₂;
H-Inp-D-2Nal-D-Trp-Pff-NH₂;
H-Apc-D-1Nal-D-Trp-3Thi-NH₂;
H-Apc-D-1Nal-D-Trp-2Fua-NH₂;
H-Apc-D-1Nal-D-Trp-Pff-NH₂;
H-Apc-D-1Nal-D-Trp-Pal-NH₂;
H-Apc-D-1Nal-D-Trp-3Pal-NH₂;
H-Apc-D-1Nal-D-Trp-2Pal-NH₂;
H-Apc-D-2Nal-D-Trp-3Thi-NH₂;
H-Apc-D-2Nal-D-Trp-2Fua-NH₂;
H-Apc-D-2Nal-D-Trp-Pff-NH₂;
H-Apc-D-2Nal-D-Trp-4Pal-NH₂;
H-Apc-D-2Nal-D-Trp-3Pal-NH₂;
H-Apc-D-2Nal-D-Trp-2Pal-NH₂;

H-Inp-D-Bip-D-Trp-Taz-NH$_2$;
H-Inp-D-Bip-D-Trp-2Fua-NH$_2$;
H-Inp-D-Bip-D-Trp-Pff-NH$_2$;
H-Inp-D-Bip-D-Bal-Taz-NH$_2$;
H-Inp-D-Bip-D-Bal-2Fua-NH$_2$; or
H-Inp-D-Bip-D-Bal-Pff-NH$_2$;
or a pharmaceutically acceptable salt thereof.

A preferred Group 2A compound, termed a Group 2B compound, is a compound according to the formula:
H-Inp-D-1Nal-D-Trp-3Pal-Lys-NH$_2$;
H-Inp-D-2Nal-D-Trp-4Pal-Lys-NH$_2$;
H-Inp-D-2Nal-D-Trp-Orn-Lys-NH$_2$;
H-Inp-D-Bip-D-Trp-Phe-Lys-NH$_2$;
H-Inp-D-2Nal-D-Trp-Thr(Bzl)-Lys-NH$_2$;
H-Inp-D-2Nal-D-Trp-Pff-Lys-NH$_2$;
H-Inp-D-2Nal-D-Trp-2Thi-Lys-NH$_2$;
H-Inp-D-2Nal-D-Trp-Taz-Lys-NH$_2$;
H-Inp-D-Dip-D-Trp-Phe-Lys-NH$_2$;
H-Inp-D-Bpa-D-Trp-Phe-Lys-NH$_2$;
H-Inp-D-2Nal-D-Bpa-Phe-Lys-NH$_2$;
H-Inp-D-1Nal-D-Trp(Ψ)-Pim;
H-Inp-D-2Nal-D-Trp-Thr(Bzl)-NH$_2$;
H-Inp-D-2Nal-D-Trp-Pff-NH$_2$;
H-Inp-D-2Nal-D-Trp(Ψ)-Pim;
H-Inp-D-Trp-D-2Nal(Ψ)-Pim;
H-Inp-D-2Nal-D-Trp-Taz-NH$_2$;
H-Inp-D-2Nal-D-Dip-Phe-NH$_2$;
H-Inp-D-2Nal-D-Trp-3Pal-Lys-NH$_2$;
H-Inp-D-Bal-D-Trp-Phe-Lys-NH$_2$;
H-Inp-D-Bal-D-Trp-2Thi-Lys-NH$_2$;
H-Inp-D-Bal-D-Trp-Taz-Lys-NH$_2$;
H-Inp-D-Bal-D-Trp-Phe-Apc-NH$_2$;
H-Inp-D-Bal-D-Trp-Taz-Apc-NH$_2$;
H-Apc-D-Bal-D-Trp-Phe-Lys-NH$_2$;
H-Apc-D-Bal-D-Trp-2Thi-Lys-NH$_2$;
H-Apc-D-Bal-D-Trp-Taz-Lys-NH$_2$;
H-Apc-D-Bal-D-1Nal-Phe-Lys-NH$_2$;
H-Apc-D-Bal-D-2Nal-Phe-Lys-NH$_2$;
H-Inp-D-1Nal-D-Trp-2Thi-Lys-NH$_2$;
H-Inp-D-1Nal-D-Trp-Taz-Lys-NH$_2$;
H-Inp-D-2Nal-D-Trp-Phe-Apc-NH$_2$;
H-Inp-D-1Nal-D-Trp-Taz-Apc-NH$_2$;
H-Inp-D-1Nal-D-Trp-Phe-Apc-NH$_2$;
H-Apc-D-1Nal-D-Trp-2Thi-Lys-NH$_2$;
H-Apc-D-1Nal-D-Trp-Taz-Lys-NH$_2$;
H-Apc-D-1Nal-D-1Nal-Phe-Lys-NH$_2$;
H-Apc-D-2Nal-D-Trp-Phe-Lys-NH$_2$;
H-Apc-D-Bal-D-Trp-Phe-Apc-NH$_2$;
H-Apc-D-Bal-D-Trp-Taz-Apc-NH$_2$;
H-Apc-D-Bal-D-1Nal-Phe-Apc-NH$_2$;
H-Apc-D-Bal-D-2Nal-Phe-Apc-NH$_2$;
H-Apc-D-1Nal-D-Trp-Taz-Apc-NH$_2$;
H-Apc-D-1Nal-D-Trp-Phe-Apc-NH$_2$;
H-Apc-D-1Nal-D-1Nal-Phe-Apc-NH$_2$;
H-Apc-D-1Nal-D-2Nal-Phe-Apc-NH$_2$;
H-Inp-D-Bal-D-Trp(Ψ)-Pim;
H-Apc-D-Bal-D-Trp-Phe-NH$_2$;
H-Apc-D-Bal-D-Trp-2Thi-NH$_2$;
H-Apc-D-Bal-D-Trp-Taz-NH$_2$;
H-Apc-D-1Nal-D-Trp-2Thi-NH$_2$;
H-Apc-D-1Nal-D-Trp-Taz-NH$_2$;
H-Apc-D-2Nal-D-Trp-2Thi-NH$_2$;
H-Apc-D-2Nal-D-Trp-Taz-NH$_2$; or
H-Aib-D-Ser(Bzl)-D-Trp(Ψ)-Pim;
or a pharmaceutically acceptable salt thereof.

A preferred Group 2B compound, termed a Group 2B-1 compound, is a compound according to the formula:
H-Inp-D-1Nal-D-Trp-3Pal-Lys-NH$_2$;
H-Inp-D-2Nal-D-Trp-4Pal-Lys-NH$_2$;
H-Inp-D-Bip-D-Trp-Phe-Lys-NH$_2$;
H-Inp-D-2Nal-D-Trp-Thr(Bzl)-Lys-NH$_2$;
H-Inp-D-2Nal-D-Trp-2Thi-Lys-NH$_2$;
H-Inp-D-2Nal-D-Trp-Taz-Lys-NH$_2$;
H-Inp-D-2Nal-D-Trp-Phe-Lys-NH$_2$;
H-Inp-D-2Nal-D-Trp-Thr(Bzl)-NH$_2$;
H-Inp-D-2Nal-D-Trp-Taz-NH$_2$;
H-Inp-D-2Nal-D-Trp-3Pal-Lys-NH$_2$;
H-Inp-D-Bal-D-Trp-2Thi-Lys-NH$_2$;
H-Inp-D-Bal-D-Trp-Phe-Lys-NH$_2$;
H-Inp-D-1Nal-D-Trp-2Thi-Lys-NH$_2$;
H-Inp-D-2Nal-D-Trp-Phe-Apc-NH$_2$;
H-Inp-D-1Nal-D-Trp-Phe-Apc-NH$_2$;
H-Inp-D-Bal-D-Trp-Phe-Apc-NH$_2$;
H-Apc-D-2Nal-D-Trp-Phe-Lys-NH$_2$;
H-Apc-D-1Nal-D-Trp-2Thi-Lys-NH$_2$;
H-Inp-D-1Nal-D-Trp-Taz-Lys-NH$_2$;
H-Inp-D-Bal-D-Trp-Taz-Lys-NH$_2$;
H-Apc-D-1Nal-D-Trp-Taz-Lys-NH$_2$;
H-Apc-D-Bal-D-Trp-Taz-Lys-NH$_2$;
H-Apc-D-Bal-D-Trp-2Thi-Lys-NH$_2$;
H-Apc-D-Bal-D-Trp-Phe-Lys-NH$_2$;
H-Apc-D-1Nal-D-Trp-Phe-Apc-NH$_2$;
H-Apc-D-Bal-D-Trp-Phe-Apc-NH$_2$;
H-Apc-D-1Nal-D-1Nal-Phe-Apc-NH$_2$;
H-Apc-D-1Nal-D-2Nal-Phe-Apc-NH$_2$;
H-Apc-D-1Nal-D-1Nal-Phe-Lys-NH$_2$;
H-Apc-D-Bal-D-1Nal-Phe-Apc-NH$_2$;
H-Apc-D-Bal-D-2Nal-Phe-Apc-NH$_2$;
H-Apc-D-Bal-D-1Nal-Phe-Lys-NH$_2$;
H-Apc-D-Bal-D-2Nal-Phe-Lys-NH$_2$;
H-Apc-D-1Nal-D-Trp-2Thi-NH$_2$;
H-Apc-D-Bal-D-Trp-Phe-NH$_2$;
H-Apc-D-1Nal-D-Trp-Taz-NH$_2$;
H-Apc-D-Bal-D-Trp-2Thi-NH$_2$;
H-Apc-D-Bal-D-Trp-Taz-NH$_2$;
H-Apc-D-2Nal-D-Trp-2Thi-NH$_2$;
H-Apc-D-2Nal-D-Trp-Taz-NH$_2$;
H-Inp-D-1Nal-D-Trp-Taz-Apc-NH$_2$;
H-Inp-D-Bal-D-Trp-Taz-Apc-NH$_2$;
H-Apc-D-1Nal-D-Trp-Taz-Apc-NH$_2$; or
H-Apc-D-Bal-D-Trp-Taz-Apc-NH$_2$;
or a pharmaceutically acceptable salt thereof.

A preferred Group 2B-1 compound, termed a Group 2B-1a compound, is a compound according to the formula:
H-Inp-D-1Nal-D-Trp-3Pal-Lys-NH$_2$;
H-Inp-D-2Nal-D-Trp-2Thi-Lys-NH$_2$;
H-Inp-D-2Nal-D-Trp-Taz-Lys-NH$_2$;
H-Inp-D-2Nal-D-Trp-Phe-Lys-NH$_2$;
H-Inp-D-Bal-D-Trp-2Thi-Lys-NH$_2$;
H-Inp-D-Bal-D-Trp-Phe-Lys-NH$_2$;
H-Inp-D-1Nal-D-Trp-2Thi-Lys-NH$_2$;
H-Inp-D-2Nal-D-Trp-Phe-Apc-NH$_2$;
H-Inp-D-1Nal-D-Trp-Phe-Apc-NH$_2$;
H-Inp-D-Bal-D-Trp-Phe-Apc-NH$_2$;
H-Apc-D-2Nal-D-Trp-Phe-Lys-NH$_2$;
H-Apc-D-1Nal-D-Trp-2Thi-Lys-NH$_2$;
H-Inp-D-1Nal-D-Trp-Taz-Lys-NH$_2$;
H-Inp-D-Bal-D-Trp-Taz-Lys-NH$_2$;
H-Apc-D-1Nal-D-Trp-Taz-Lys-NH$_2$;
H-Apc-D-Bal-D-Trp-Taz-Lys-NH$_2$;
H-Apc-D-Bal-D-Trp-2Thi-Lys-NH$_2$;
H-Apc-D-Bal-D-Trp-Phe-Lys-NH$_2$;

H-Apc-D-1Nal-D-Trp-Phe-Apc-NH$_2$;
H-Apc-D-Bal-D-Trp-Phe-Apc-NH$_2$;
H-Apc-D-Bal-D-2Nal-Phe-Lys-NH$_2$;
H-Apc-D-1Nal-D-Trp-2Thi-NH$_2$;
H-Apc-D-Bal-D-Trp-Phe-NH$_2$;
H-Apc-D-Bal-D-Trp-2Thi-NH$_2$;
H-Apc-D-2Nal-D-Trp-2Thi-NH$_2$;
H-Inp-D-1Nal-D-Trp-Taz-Apc-NH$_2$;
H-Inp-D-Bal-D-Trp-Taz-Apc-NH$_2$;
H-Apc-D-1Nal-D-Trp-Taz-Apc-NH$_2$;
H-Apc-D-Bal-D-Trp-Taz-Apc-NH$_2$; or or a pharmaceutically acceptable salt thereof.

A more preferred Group 2B-1 compound, termed a Group 2B-1b compound, is a compound according to the formula:
H-Inp-D-2Nal-D-Trp-2Thi-Lys-NH$_2$;
H-Inp-D-2Nal-D-Trp-Phe-Lys-NH$_2$;
H-Inp-D-Bal-D-Trp-2Thi-Lys-NH$_2$;
H-Inp-D-Bal-D-Trp-Phe-Lys-NH$_2$;
H-Inp-D-1Nal-D-Trp-2Thi-Lys-NH$_2$;
H-Inp-D-1Nal-D-Trp-Phe-Apc-NH$_2$;
H-Inp-D-Bal-D-Trp-Phe-Apc-NH$_2$;
H-Apc-D-2Nal-D-Trp-Phe-Lys-NH$_2$;
H-Apc-D-1Nal-D-Trp-2Thi-Lys-NH$_2$;
H-Inp-D-Bal-D-Trp-Taz-Lys-NH$_2$;
H-Apc-D-1Nal-D-Trp-Taz-Lys-NH$_2$;
H-Apc-D-Bal-D-Trp-Taz-Lys-NH$_2$;
H-Apc-D-Bal-D-Trp-2Thi-Lys-NH$_2$;
H-Apc-D-Bal-D-Trp-Phe-Lys-NH$_2$;
H-Apc-D-1Nal-D-Trp-Phe-Apc-NH$_2$; or
H-Apc-D-2Nal-D-Trp-2Thi-NH$_2$;

or a pharmaceutically acceptable salt thereof.

A still more preferred Group 2B-1 compound, termed a Group 2B-1c compound, is a compound according to the formula:
H-Inp-D-2Nal-D-Trp-2Thi-Lys-NH$_2$;
H-Inp-D-Bal-D-Trp-Phe-Apc-NH$_2$;
H-Apc-D-1Nal-D-Trp-2Thi-Lys-NH$_2$;
H-Apc-D-1Nal-D-Trp-Taz-Lys-NH$_2$;

or a pharmaceutically acceptable salt thereof.

A particularly preferred Group 2B-1c compound is a compound according to the formula:
H-Inp-D-Bal-D-Trp-Phe-Apc-NH$_2$;

or a pharmaceutically acceptable salt thereof.

Another still more preferred Group 2B-1 compound, termed a Group 2B-1d compound, is a compound according to the formula:
H-Inp-D-Bal-D-Trp-Taz-Lys-NH$_2$;
H-Apc-D-1Nal-D-Trp-Taz-Lys-NH$_2$;
H-Apc-D-Bal-D-Trp-Taz-Lys-NH$_2$;
H-Apc-D-1Nal-D-Trp-Phe-Apc-NH$_2$; or or a pharmaceutically acceptable salt thereof.

Another preferred Group 2B compound, termed a Group 2B-2 compound, is a compound according to the formula:
H-Inp-D-2Nal-D-Trp-Orn-Lys-NH$_2$;
H-Inp-D-2Nal-D-Trp-Pff-Lys-NH$_2$;
H-Inp-D-Dip-D-Trp-Phe-Lys-NH$_2$;
H-Inp-D-Bpa-D-Trp-Phe-Lys-NH$_2$;
H-Inp-D-2Nal-D-Bpa-Phe-Lys-NH$_2$;
H-Inp-D-2Nal-D-Trp-Pff-NH$_2$;
H-Inp-D-2Nal-D-Dip-Phe-NH$_2$;
H-Inp-D-Trp-D-2Nal(Ψ)-Pim;
H-Inp-D-2Nal-D-Trp(Ψ)-Pim;
H-Inp-D-1Nal-D-Trp(Ψ)-Pim;
H-Inp-D-Bal-D-Trp(Ψ)-Pim; or
H-Aib-D-Ser(Bzl)-D-Trp(Ψ)-Pim;

or a pharmaceutically acceptable salt thereof.

A preferred Group 2B-2 compound, termed a Group 2B-2a compound, is a compound according to the formula:
H-Inp-D-2Nal-D-Trp-Pff-Lys-NH$_2$;
H-Inp-D-Dip-D-Trp-Phe-Lys-NH$_2$;
H-Inp-D-2Nal-D-Trp-Pff-NH$_2$;
H-Inp-D-1Na-D-Trp(Ψ)-Pim; or
H-Inp-D-Bal-D-Trp(Ψ)-Pim;

or a pharmaceutically acceptable salt thereof.

Another preferred Group 2 compound, termed a Group 2C compound, is a compound according to the formula:
H-Inp-D-2Nal-D-Trp-3Pal-NH$_2$;
H-Inp-D-2Nal-D-Trp-4Pal-NH$_2$;
H-Inp-D-1Nal-D-Trp-3Pal-NH$_2$;
H-Inp-D-Bip-D-Trp-Phe-NH$_2$;
H-Inp-D-2Nal-D-Trp-2Thi-NH$_2$;
H-Inp-D-2Nal-D-Trp-3Thi-NH$_2$;
H-Inp-D-Dip-D-Trp-Phe-NH$_2$;
H-Inp-D-Bal-D-Trp-Phe-NH$_2$;
H-Inp-D-2Nal-D-Bal-Phe-NH$_2$;
H-Inp-D-1Nal-D-Trp-2Thi-NH$_2$; or
H-Apc-D-1Nal-D-Trp-Phe-NH$_2$;

or a pharmaceutically acceptable salt thereof.

A preferred Group 2C compound, termed a Group 2C-1 compound, is a compound according to the formula:
H-Inp-D-2Nal-D-Trp-2Thi-NH$_2$;
H-Inp-D-Bal-D-Trp-Phe-NH$_2$;
H-Inp-D-1Nal-D-Trp-2Thi-NH$_2$; or
H-Apc-D-1Nal-D-Trp-Phe-NH$_2$;

or a pharmaceutically acceptable salt thereof.

A particularly preferred compound of the invention, termed a Group 3 compound, is a compound according to the formula:
H-Inp-D-1Nal-D-Trp-2Thi-Apc-NH$_2$;
H-Inp-D-Bal-D-Trp-2Thi-Apc-NH$_2$;
H-Apc-D-1Nal-D-Trp-2Thi-Apc-NH$_2$;
H-Apc-D-Bal-D-Trp-2Thi-Apc-NH$_2$; or
H-Apc-D-1Nal-D-Trp-Phe-Lys-NH$_2$;

or a pharmaceutically acceptable salt thereof.

In another aspect the invention features a method of determining a compound's ability to bind to a GHS receptor, said method comprising the step of measuring the ability of a compound to affect binding of a compound according to formula (I) or according to any one of Groups 1, 1A, 2, 2A, 2B, 2B-1, 2B-1a, 2B-1b, 2B-1c, 2B-1d, 2B-2, 2B-2a, 2C, or 2C-1 to said receptor, to a fragment of said receptor, to a polypeptide comprising said fragment of said receptor, or to a derivative of said polypeptide.

In another aspect the invention features a method for achieving a beneficial affect in a subject comprising, said method comprising the step of administering to said subject an effective amount of a compound according to formula (I), Group 1, Group 1A, Group 2, Group 2A, Group 2B, Group 2B-1, Group 2B-1a, Group 2B-1b, Group 2B-1c, Group 2B-1d, Group 2B-2, Group 2B-2a, Group 2C, or Group 2C-1, or a pharmaceutically acceptable salt thereof, wherein said effective amount is effective for producing a beneficial effect in helping to treat (e.g., cure or reduce the severity) or prevent (e.g., reduce the likelihood of onset or severity) a disease or disorder.

In another aspect the invention features a method for stimulating growth hormone secretion in a subject in need of such stimulation, comprising the step of administering to a subject an effective amount of a ghrelin agonist according to formula (I), Group 1, Group 1A, Group 2, Group 2A, Group 2B, Group 2B-1, Group 2B-1a, Group 2B-1b, Group 2B-1c, Group 2B-1d, Group 2B-2, Group 2B-2a, Group 2C, or Group 2C-1, or a pharmaceutically acceptable salt thereof, wherein said effective amount is at least an amount sufficient to produce a detectable increase in growth hormone secretion and, preferably, is an amount sufficient to achieve a beneficial affect in a patient.

In one embodiment of the immediately foregoing aspect said stimulation of growth hormone secretion is indicated for treatment of a growth hormone deficient state, for increasing muscle mass, for increasing bone density, for sexual dysfunction in males or females, for facilitating a weight gain, for facilitating maintenance of weight, for facilitating maintenance of physical functioning, for facilitating recovery of physical function, and/or facilitating appetite increase. Preferably said facilitating weight gain, facilitating maintenance in weight, and/or facilitating appetite increase is indicated in a patient having a disease or disorder, or under going a treatment, accompanied by weight loss. More preferably said diseases or disorders accompanied by weight loss include anorexia, bulimia, cancer cachexia, AIDS, (e.g., wasting), cachexia, and wasting in frail elderly. Also preferably said treatments accompanied by weight loss include chemotherapy, radiation therapy, temporary or permanent immobilization, and dialysis.

In another aspect the invention features a method for suppressing growth hormone secretion in a subject in need of such suppression, comprising the step of administering to a subject an effective amount of a ghrelin antagonist according to formula (I), Group 1, Group 1A, Group 2, Group 2A, Group 2B, Group 2B-1, Group 2B-1a, Group 2B-1b, Group 2B-1c, Group 2B-1d, Group 2B-2, Group 2B-2a, Group 2C, or Group 2C-1, or a pharmaceutically acceptable salt thereof, wherein said effective amount is at least an amount sufficient to produce a detectable decrease in growth hormone secretion and, preferably, is an amount sufficient to achieve a beneficial affect in a patient.

In one embodiment of the immediately foregoing aspect said suppression of growth hormone secretion is indicated for the treatment of a disease or condition characterized by excessive growth hormone secretion, for facilitation of weight loss, for facilitation of appetite decrease, for facilitation of weight maintenance, for treating obesity, for treating diabetes, for treating complications of diabetes including retinopathy, and/or for treating cardiovascular disorders.

In a preferred embodiment of the immediately foregoing aspect excessive weight is a contributing factor to a disease or condition including hypertension, diabetes, dyslipidemia, cardiovascular disease, gall stones, osteoarthritis and cancers. More preferably said facilitation of weight loss reduces the likelihood of such diseases or conditions. Also more preferably said facilitation of weight loss comprises at least part of a treatment for such diseases or conditions.

A method of eliciting a ghrelin agonist effect in a subject, comprising the step of administering to a subject an effective amount of one or more of a ghrelin agonist according to formula (I), Group 1, Group 1A, Group 2, Group 2A, Group 2B, Group 2B-1, Group 2B-1a, Group 2B-1b, Group 2B-1c, Group 2B-1d, Group 2B-2, Group 2B-2a, Group 2C, or Group 2C-1, or a pharmaceutically acceptable salt thereof, wherein said effective amount is at least an amount sufficient to produce a detectable increase in growth hormone secretion and, preferably, is an amount sufficient to achieve a beneficial affect in a patient.

In another aspect the invention features a method of eliciting a ghrelin antagonist effect in a subject, comprising the step of administering to a subject an effective amount of one or more of a ghrelin antagonist according to formula (I), Group 1, Group 1A, Group 2, Group 2A, Group 2B, Group 2B-1, Group 2B-1a, Group 2B-1b, Group 2B-1c, Group 2B-1d, Group 2B-2, Group 2B-2a, Group 2C, or Group 2C-1, or a pharmaceutically acceptable salt thereof, wherein said effective amount is at least an amount sufficient to produce a detectable decrease in growth hormone secretion and, preferably, is an amount sufficient to achieve a beneficial affect in a patient.

Compounds of the invention are active at the GHS receptor. The compounds can bind to the receptor, and preferably, stimulate receptor activity. Thus a compound of the invention is useful as a functional ghrelin analog, both as a research tool and/or as a therapeutic agent.

Research tool applications generally involve the use of a compound of the invention and the presence of a GHS receptor or fragment thereof. The GHS receptor can be present in different environments such as a mammalian subject, a whole cell, or a cell membrane fragment Examples of research tool applications include screening for compounds active at the GHS receptor, determining the presence of the GHS receptor in a sample or preparation, and examining the role or effect of ghrelin.

One aspect of the present invention features a method of screening for ghrelin agonists and/or for ghrelin antagonists. Screening for ghrelin agonists can be performed, for example, by using a compound according to formula (I), Group 1, Group 1A, Group 2, Group 2A, Group 2B, Group 2B-1, Group 2B-1a, Group 2B-1b, Group 2B-1c, Group 2B-1d, Group 2B-2, Group 2B-2a, Group 2C, or Group 2C-1, or a pharmaceutically acceptable salt thereof, in a competition experiment with test compounds. Screening for ghrelin antagonists can be performed, for example, by using a compound according to formula (I), Group 1, Group 1A, Group 2, Group 2A, Group 2B, Group 2B-1, Group 2B-1a, Group 2B-1b, Group 2B-1c, Group 2B-1d, Group 2B-2, Group 2B-2a, Group 2C, or Group 2C-1, or a pharmaceutically acceptable salt thereof, to produce GHS receptor activity and then measuring the ability of a test compound to alter GHS receptor activity.

Another aspect of the present invention features a method of screening for a compound able to bind to a GHS receptor. The method comprises the step of measuring the ability of a test compound to affect the binding of a compound according to formula (I), Group 1, Group 1A, Group 2, Group 2A, Group 2B, Group 2B-1, Group 2B-1a, Group 2B-1b, Group 2B-1c, Group 2B-1d, Group 2B-2, Group 2B-2a, Group 2C, or Group 2C-1, or a pharmaceutically acceptable salt thereof, to either the receptor, a fragment of the receptor comprising a ghrelin binding site, a polypeptide comprising the fragment, or a derivative of the polypeptide.

Ghrelin agonists can be used to achieve a beneficial effect in a subject. For example, ghrelin induces growth hormone release from primary-culture pituitary cells in a dose-dependent manner without stimulating the release of the other pituitary hormones. Injected intravenously into anaesthetized rats, ghrelin stimulated pulsatile release of growth hormone. (Kojima et al. *Nature* 1999, 402, 656-660.) Thus a non-exclusive list of examples wherein such a beneficial effect may be indicated would include: treating a growth hormone deficient state, increasing muscle mass, increasing bone density, treating sexual dysfunction in males or females, facilitating a weight gain, facilitating maintenance of weight, facilitating maintenance of physical functioning, facilitating recovery of physical function, and/or facilitating appetite increase. Facilitating a weight gain, maintenance in weight, or appetite increase is particularly useful for a subject having a disease or disorder, or undergoing a treatment, accompanied by weight loss. Diseases or disorders accompanied by weight loss include, e.g., anorexia, bulimia, cancer cachexia, AIDS, (e.g., wasting), cachexia, wasting in frail elderly, and the like. Treatments accompanied by weight loss include, e.g., chemotherapy, radiation therapy, temporary or permanent immobilization, dialysis, and the like.

Thus another aspect of the present invention features a method for achieving a beneficial affect in a subject, said method comprising the step of administering to said subject an effective amount of one or more of a compound according to formula (I), Group 1, Group 1A, Group 2, Group 2A, Group 2B, Group 2B-1, Group 2B-1a, Group 2B-1b, Group 2B-1c, Group 2B-1d, Group 2B-2, Group 2B-2a, Group 2C, or Group 2C-1, or a pharmaceutically acceptable salt thereof, wherein said effective amount is effective for producing a beneficial effect in helping to treat (e.g., cure or reduce the severity of) or prevent (e.g., reduce the likelihood of onset or severity of) a disease or disorder.

In a preferred embodiment of the immediately preceding method said beneficial affect comprises stimulating growth hormone secretion in a subject in need of such stimulation, comprising the step of administering to a subject an effective amount of one or more of a compound according to formula (I), Group 1, Group 1A, Group 2, Group 2A, Group 2B, Group 2B-1, Group 2B-1a, Group 2B-1b, Group 2B-1c, Group 2B-1d, Group 2B-2, Group 2B-2a, Group 2C, or Group 2C-1, or a pharmaceutically acceptable salt thereof, wherein said effective amount is at least an amount sufficient to produce a detectable increase in growth hormone secretion and, preferably, is an amount sufficient to achieve a beneficial affect in a patient.

In a more preferred embodiment of the immediately preceding method said stimulation of growth hormone secretion is indicated for treatment of a growth hormone deficient state, for increasing muscle mass, for increasing bone density, for sexual dysfunction in males or females, for facilitating a weight gain, for facilitating maintenance of weight, for facilitating maintenance of physical functioning, for facilitating recovery of physical function, and/or facilitating appetite increase.

In another preferred embodiment of the immediately preceding method said facilitating weight gain, facilitating maintenance in weight, and/or facilitating appetite increase is indicated in a patient having a disease or disorder, or under going a treatment, accompanied by weight loss. More preferably said diseases or disorders accompanied by weight loss include anorexia, bulimia, cancer cachexia, AIDS, (e.g., wasting), cachexia, and wasting in frail elderly.

In another more preferred embodiment of the immediately preceding method said treatments accompanied by weight loss include chemotherapy, radiation therapy, temporary or permanent immobilization, and dialysis.

Ghrelin antagonists can also be used to achieve a beneficial effect in a patient. For example, a ghrelin antagonist can be used to facilitate weight loss, facilitate appetite decrease, facilitate weight maintenance, treat obesity, treat diabetes, treat complications of diabetes including retinopathy, and/or treat cardiovascular disorders. Excessive weight is a contributing factor to different diseases including hypertension, diabetes, dyslipidemias, cardiovascular disease, gall stones, osteoarthritis and certain forms of cancers. Bringing about a weight loss can be used, for example, to reduce the likelihood of such diseases and as part of a treatment for such diseases.

Compounds of the invention may also antagonize the effects of ghrelin in vitro and in vivo. Thus yet another aspect of the present invention features a method for suppressing growth hormone secretion in a subject in need of such suppression, comprising the step of administering to a subject an effective amount of one or more of a compound according to formula (I), Group 1, Group 1A, Group 2, Group 2A, Group 2B, Group 2B-1, Group 2B-1a, Group 2B-1b, Group 2B-1c, Group 2B-1d, Group 2B-2, Group 2B-2a, Group 2C, or Group 2C-1, or a pharmaceutically acceptable salt thereof, wherein said effective amount is at least an amount sufficient to produce a detectable decrease in growth hormone secretion and, preferably, is an amount sufficient to achieve a beneficial affect in a patent.

In a preferred embodiment of the immediately preceding method said suppression of growth hormone secretion is indicated for the treatment of a disease or condition characterized by excessive growth hormone secretion, for facilitation of weight loss, for facilitation of appetite decrease, for facilitation of weight maintenance, for treating obesity, for treating diabetes, for treating complications of diabetes including retinopathy, and/or for treating cardiovascular disorders.

In a more preferred embodiment of the immediately preceding method excessive weight is a contributing factor to a disease or condition including hypertension, diabetes, dyslipidemia, cardiovascular disease, gall stones, osteoarthritis and cancers.

In another more preferred embodiment of the immediately preceding method said facilitation of weight loss reduces the likelihood of such diseases or conditions and/or said facilitation of weight loss comprises at least part of a treatment for such diseases or conditions.

As is also appreciated by those of skill in the art, ghrelin and agonists thereof may also be used to achieve beneficial cardiovascular effects. (Nagaya, et al., Regul Pept. 2003 Jul. 15: 114(2-3): 71-77.) For example, it is known that ghrelin inhibits apoptosis of cardiomyocytes and endothelial cells in vitro, that repeated administration of ghrelin improves cardiac structure and function and attenuates the development of cardiac cachexia in rats with heart failure, and that ghrelin decreases systemic vascular resistance and increases cardiac output in human patients with heart failure. (Id.) Thus it has been recognized that ghrelin and ghrelin agonists represent potential therapeutics for the treatment of severe chronic heart failure.

In a particularly preferred embodiment of each of the methods of using a ghrelin agonist described herein the ghrelin agonist is a compound according to the formula:

H-Inp-D-Bal-D-Trp-Phe-Apc-NH$_2$;

or a pharmaceutically acceptable salt thereof.

A compound or compounds of the invention can be administered to a subject. A "subject" refers to a mammalian or non-mammalian animal including, for example and without limitation, a human, a rat, a mouse, or a farm animal. Reference to subject does not necessarily indicate the presence of a disease or disorder. Thus the term subject further includes, for example, a mammalian or non-mammalian animal being dosed with a ghrelin analog as part of an experiment, a mammalian or non-mammalian animal being treated to help alleviate a disease or disorder, and a mammalian or non-mammalian animal being treated prophylactically to retard or prevent the onset of a disease or disorder.

Other features and advantages of the present invention are apparent from the additional descriptions provided herein including the different examples. The provided examples Illustrate different components and methodology useful in practicing the present invention. The examples do not limit the claimed invention. Based on the present disclosure the skilled artisan can identify and employ other components and methodology useful for practicing the present invention.

Unless otherwise stated, those amino acids with a chiral center are provided in the L-enantiomer. Reference to "a derivative thereof" refers to a modified amino acid such as the corresponding D-amino acid, a N-alkyl-amino acid, a β-amino acid, or a labeled amino acid.

DETAILED DESCRIPTION OF THE INVENTION

The present invention features peptidyl analogs active at the GHS receptor. Human ghrelin is a 28 amino acid modified peptide where a serine hydroxyl group is esterified by n-octanoic acid. (Kojima et al. Nature 1999, 402, 656-660, and Kojima, (Abstract), Third International Symposium on Growth Hormone Secretagogues, Keystone, Colo., USA 2000, Feb. 17-19.)

Certain amino acids present in compounds of the invention are represented herein as follows:
A3c 1-amino-1-cyclopropanecarboxylic acid
A4c 1-amino-1-cyclobutanecarboxylic acid
A5c 1-amino-1-cyclopentanecarboxylic acid
A6c 1-amino-1-cyclohexanecarboxylic acid
Abu α-aminobutyric acid
Acc 1-amino-1-cyclo($C_3$-$C_9$)alkyl carboxylic acid
Act 4-amino-4-carboxytetrahydropyran, i.e.:

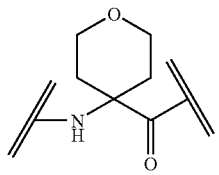

Aib α-aminoisobutyric acid
Ala or A alanine
β-Ala beta-alanine
Apc amino piperidinylcarboxylic acid, i.e.:

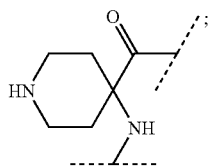

Arg or R arginine
hArg homoarginine
Asn or N asparagine
Asp or D aspartic acid
Bal 3-Benzothienylalanine, i.e.:

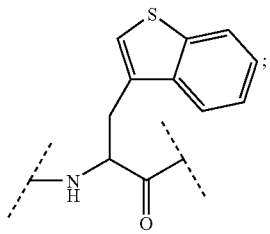

Bip 4,4'-Biphenylalanine, i.e.:

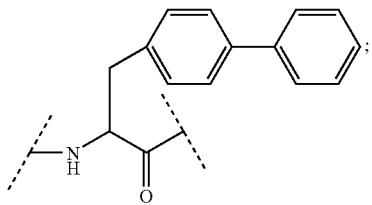

Bpa 4-Benzoylphenylalanine, i.e.:

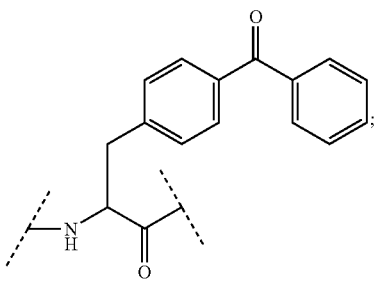

Cha β-cyclohexylalanine;
Cys or C cysteine;
Dab 2,4-diaminobutyric acid, (α,γ-Diaminobutyric acid);
Dap 2,3-diaminopropionic acid, (α,β-Diaminopropionic acid);
Dip β,β-Diphenylalanine, i.e.:

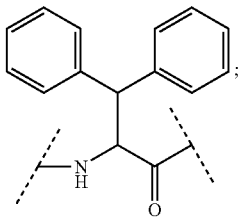

Dhp 3,4-dehydroproline
Dmt 5,5-dimethylthiazolidine-4-carboxylic acid
2Fua β-(2-furyl)-alanine, i.e.:

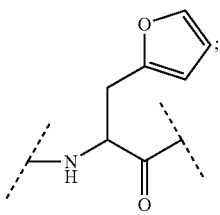

Gln or Q glutamine
Glu or E glutamic acid
Gly or G glycine
His or H histidine
3Hyp trans-3-hydroxy-L-proline, i.e., (2S,3S)-3-hydroxypyrrolidine-2-carboxylic acid;
4Hyp 4-hydroxyproline, i.e., (2S,4R)hydroxypyrrolidine-2-carboxylic acid;
Ile or I isoleucine
Inc indoline-2-carboxylic acid
Inp isonipecotic acid, i.e.:

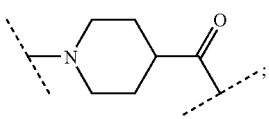

Ktp 4-ketoproline
Leu or L leucine
hLeu homoleucine
Lys or K lysine
Met or M methionine
1Nal β-(1-Naphthyl)alanine:
2Nal β-(2-Naphthyl)alanine;
Nle norleucine
Nva norvaline
Oic octahydroindole-2-carboxylic acid
Orn ornithine
2Pal β-2-Pyridyl)-alanine, i.e.,

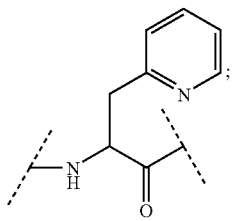

3Pal β-(3-Pyridyl)-alanine, i.e.:

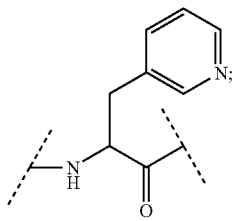

4Pal β-(4-Pyridyl)-alanine, i.e.:

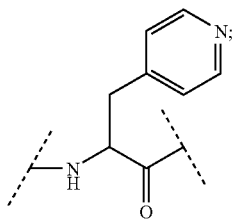

Pff pentafluorophenylalanine, i.e.

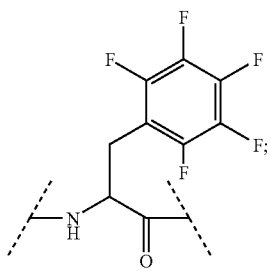

Phe or F phenylalanine
hPhe homophenylalanine
Pim 2'-(4-Phenyl)imidazolyl, i.e.:

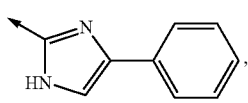

Pip pipecolic acid
Pro or P proline
Ser or S serine

Taz β-(4-thiazolyl)alanine, i.e.,

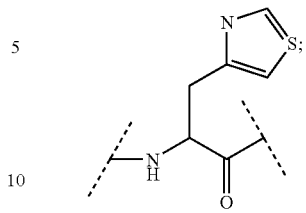

2Thi β-(2-thienyl)alanine, i.e.:

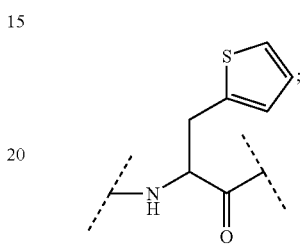

3Thi β-(3-thienyl)alanine, i.e.:

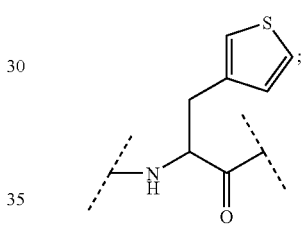

Thr or T threonine
Thz thiazolidine-4-carboxylic acid
Tic 1,2,3,4-tetrahydroisoquinoline-3-carboxylic acid
Tle tert-leucine
Trp or W tryptophan
Tyr or Y tyrosine
Val or V valine
Certain other abbreviations used herein are defined as follows:
Boc: tert-butyloxycarbonyl
Bzl: benzyl
DCM: dichloromethane
DIC: N,N-diisopropylcarbodiimide
DIEA: diisopropylethyl amine
Dmab: 4-{N-(1-(4,4-dimethyl-2,6-dioxocyclohexylidene)-3-methylbutyl)-amino}benzyl
DMAP: 4-(dimethylamino)pyridine
DMF dimethylformamide
DNP: 2,4-dinitrophenyl
Fmoc: Fluorenylmethyloxycarbonyl
HBTU: 2-(1H-benzotriazole-1-yl)-1,1,3,3-tetramethyluronium hexafluorophosphate
cHex cyclohexyl
HOAT: O-(7-azabenzotriazol-1-yl)-1,1,3,3-tetramethyluronium hexafluorophosphate
HOBt: 1-hydroxy-benzotriazole
HOSu: N-hydroxysuccinimide
Mmt: 4-methoxytrityl
NMP: N-methylpyrrolidone
Pbf: 2,2,4,6,7-pentamethyldihydrobenzofuran-5-sulfonyl tBu: tert-butyl
TIS: triisopropylsilane
TOS: tosyl
trt trityl
TFA: trifluoro acetic acid
TFFH: tetramethylfluoroforamidinium hexafluorophosphate
Z: benzyloxycarbonyl Unless otherwise apparent, abbreviations (e.g. Ala) of amino acids in this disclosure stand for the structure of —NH—C(R)(R')—CO—, wherein R and R' each is, independents hydrogen or the side chain of an amino acid (e.g., R=$CH_3$ and R'=H for Ala), or R and R' may be joined to form a ring system.

"Alkyl" refers to a hydrocarbon group containing one or more carbon atoms, where multiple carbon atoms if present are joined by single bonds. The alkyl hydrocarbon group may be straight-chain or contain one or more branches or cyclic groups.

"Substituted alkyl" refers to an alkyl wherein one or more hydrogen atoms of the hydrocarbon group are replaced with one or more substituents selected from the group consisting of halogen, (i.e., fluorine, chlorine, bromine, and iodine), —OH, —CN, —SH, —$NH_2$, —$NHCH_3$, —$NO_2$, —$C_{1-2}$ alkyl substituted with 1 to 6 halogens, —$CF_3$, —$OCH_3$, —$OCF_3$, and —$(CH_2)_{0-4}$—COOH. In different embodiments 1, 2, 3 or 4 substituents are present. The presence of —$(CH_2)_{0-4}$—COOH results in the production of an alkyl acid. Examples of alkyl acids containing, or consisting of, —$(CH_2)_{0-4}$—COOH include 2-norbornane acetic acid, tert-butyric acid and 3-cyclopentyl propionic acid.

"Heteroalkyl" refers to an alkyl wherein one of more of the carbon atoms in the hydrocarbon group are replaced with one or more of the following groups: amino, amido, —O—, or carbonyl. In different embodiments 1 or 2 heteroatoms are present.

"Substituted heteroalkyl" refers to a heteroalkyl wherein one or more hydrogen atoms of the hydrocarbon group are replaced with one or more substituents selected from the group consisting of halogen, (i.e., fluorine, chlorine, bromine, and iodine), —OH, —CN, —SH, —$NH_2$, —$NHCH_3$, —$NO_2$, —$C_{1-2}$ alkyl substituted with 1 to 6 halogens, —$CF_3$, —$OCH_3$, —$OCF_3$, and —$(CH_2)_{0-4}$—COOH. In different embodiments 1, 2, 3 or 4 substituents are present.

"Alkenyl" refers to a hydrocarbon group made up of two or more carbons where one or more carbon-carbon double bonds are present. The alkenyl hydrocarbon group may be straight-chain or contain one or more branches or cyclic groups.

"Substituted alkenyl" refers to an alkenyl wherein one or more hydrogens are replaced with one or more substituents selected from the group consisting of halogen (i.e., fluorine, chlorine, bromine, and iodine), —OH, —CN, —SH, —$NH_2$, —$NHCH_3$, —$NO_2$, —$C_{1-2}$ alkyl substituted with 1 to 6 halogens, —$CF_3$, —$OCH_3$, —$OCF_3$, and —$(CH_2)_{0-4}$—COOH. In different embodiments 1, 2, 3 or 4 substituents are present.

"Aryl" refers to an optionally substituted aromatic group with at least one ring having a conjugated pi-electron system, containing up to two conjugated or fused ring systems. Aryl includes carbocyclic aryl, heterocyclic aryl and biaryl groups. Preferably, the aryl is a 5 or 6 membered ring. Preferred atoms for a heterocyclic aryl are one or more sulfur, oxygen, and/or nitrogen. Examples of aryl include phenyl, 1-naphthyl, 2-naphthyl, indole, quinoline, 2-imidazole, and 9-anthracene. Aryl substituents are selected from the group consisting of —$C_{1-4}$ alkyl, —$C_{1-4}$ alkoxy, halogen (i.e., fluorine, chlorine, bromine, and iodine), —OH, —CN, —SH, —$NH_2$, —$NO_2$, —$C_{1-2}$ alkyl substituted with 1 to 5 halogens, —$CF_3$, —$OCF_3$, and —$(CH_2)_{0-4}$—COOH. In different embodiments the aryl contains 0, 1, 2, 3, or 4 substituents.

"Alkylaryl" refers to an "alkyl" joined to an "aryl".

When a non-amino acid imidazole moiety, (e.g., Pim, defined above), is present at the C-terminus of a compound of the invention it is understood that the imidazole moiety is attached to the adjacent amino acid via a pseudo-peptide bond, wherein a bond is formed between the position 2 carbon of the imidazole ring and the alpha carbon of the amino acid. For example, in the case where the adjacent amino acid is D-tryptophan (D-Trp) and the imidazole moiety is Pim, the C-terminus of the peptide would appear as follows:

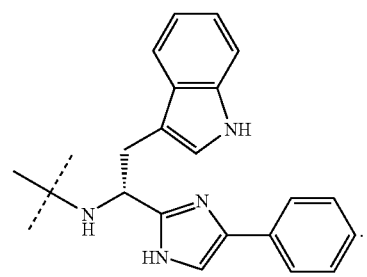

For clarity, in the written formula for such a compound the presence of this bond is indicated by the Greek letter "Ψ" alone in parentheses. For example, the written formula H-Inp-D-Trp-D-2Nal(Ψ)-Pim denotes the structure:

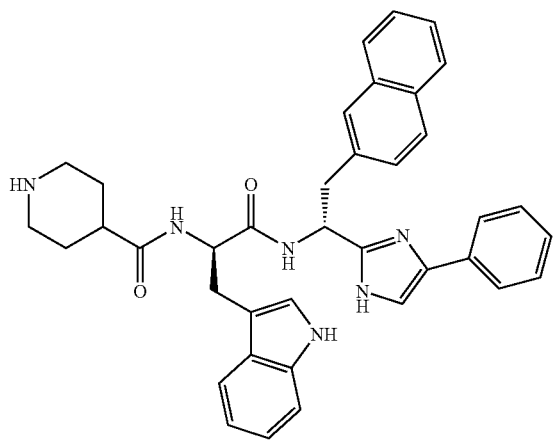 [SMILES: O=C(N[C@H](Cc1c[nH]c2ccccc12)C(=O)N[C@H](Cc1ccc2ccccc2c1)c1nc(-c2ccccc2)c[nH]1)C1CCNCC1]

The present invention includes diastereomers as well as their racemic and resolved enantiomerically pure forms. Ghrelin analogs can contain D-amino acids, L-amino acids or a combination thereof. Preferably, amino acids present in a ghrelin analog are the L-enantiomers.

Preferred derivatives of analogs of the invention comprise D-amino acids, N-alkyl-amino acids, β-amino acids, and/or one or more labeled amino acids (including a labeled version of a D-amino acid, a N-alkyl-amino acids, or a β-amino acid). A labeled derivative indicates the alteration of an amino acid or amino acid derivative with a detectable label. Examples of detectable labels include luminescent, enzymatic, and radioactive labels. Both the type of label and the position of the label can effect analog activity. Labels should be selected and positioned so as not to substantially alter the activity of the ghrelin analog at the GHS receptor. The effect of a particular label and position on ghrelin activity can be determined using assays measuring ghrelin activity and/or binding.

A protecting group covalently joined to the C-terminal carboxy group reduces the reactivity of the carboxy terminus under in vivo conditions. The carboxy terminus protecting group is preferably attached to the α-carbonyl group of the last amino acid. Preferred carboxy terminus protecting groups include amide, methylamide, and ethylamide.

EXAMPLES

Examples are provided below to further illustrate different features of the present invention. The examples also illustrate useful methodology for practicing the invention. These examples do not limit the claimed invention.

Synthesis

The compounds of the invention can be produced using the techniques disclosed in the examples herein as well as techniques that are well known in the art. For example, a polypeptide region of a GHRP analog can be chemically or biochemically synthesized and modified. Examples of techniques for biochemical synthesis involving the introduction of a nucleic acid into a cell and expression of nucleic acids are provided in Ausubel, *Current Protocols in Molecular Biology*, John Wiley, 1987-1998, and Sambrook et al., in *Molecular Cloning, A Laboratory Manual*, 2$^{nd}$ Edition, Cold Spring Harbor Laboratory Press, 1989. Techniques for chemical synthesis of polypeptides are also well known in the art. (See e.g., Vincent in *Peptide and Protein Drug Delivery*, New York, N.Y., Dekker, 1990.) For example, the peptides of this invention can be prepared by standard solid phase peptide synthesis. (See, e.g., Stewart, J. M., et al., Solid Phase Synthesis (Pierce Chemical Co., 2d ed. 1984).)

The substituent $R^1$ of the above formula (I) may be attached to the free amine of the N-terminal amino acid by standard methods known in the art. For example, alkyl groups, e.g., $(C_1-C_{30})$alkyl, may be attached using reductive alkylation. Hydroxyalkyl groups, e.g., $(C_1-C_{30})$hydroxyalkyl, may also be attached using reductive alkylation wherein the free hydroxy group is protected with a t-butyl ester. Acyl groups, e.g., $COE^1$, may be attached by coupling the free acid, e.g., $E^1COOH$, to the free amine of the N-terminal amino acid by mixing the completed resin with 3 molar equivalents of both the free acid and diisopropylcarbodiimide in methylene chloride for about one hour. If the free acid contains a free hydroxy group, e.g., p-hydroxyphenylpropionic acid, then the coupling should be performed with an additional 3 molar equivalents of HOBT.

Peptides of the invention also can be and were synthesized in a parallel fashion on an ACT 396 Multiple Biomolecular Synthesizer (Advanced ChemTech, Louisville, Ky.), ("synthesizer"), as follows. The synthesizer was programmed to perform the following reaction cycle: (1) washing with dimethylformamide (DMF), (2) removing Fmoc protecting group with 20% piperidine in DMF for 1×5 min and 1×25 min, (3) washing with DMF, (4) coupling with Fmoc amino acid for 1 h at room temperature in the presence of diisopropylcarbodiimide (DIC) and 1-hydroxybenzotriazole (HOBt), and (5) repeating step 4.

Examples 1-65

Each of the reaction wells contained 0.0675 mmol of Rink Amide MBHA resin (substitution=0.72 mmol/g, Novabiochem, San Diego, Calif.). The following Fmoc amino acids (Novabiochem, San Diego, Calif.; Chem-Impex International, Wood Dale, Ill.; SyntheTech, Albany, Oreg.; Pharma Core, High Point, N.C.) were used: Fmoc-Lys(Boc)-OH, Fmoc-Phe-OH, Fmoc-H-Inp-OH, Fmoc-D-1Nal-OH, Fmoc-D-2Nal-OH, Fmoc-D-Trp(Boc)-OH, Fmoc-3Pal-OH, Fmoc-4Pal-OH, Fmoc-Orn(Boc)-OH, Fmoc-D-Bip-OH, Fmoc-Thr(Bzl)-OH, Fmoc-Pff-OH, Fmoc-2Thi-OH, Fmoc-Taz-OH, Fmoc-D-Dip-OH, Fmoc-D-Bpa-OH, Fmoc-D-Bal-OH, and Fmoc-Apc(Boc)-OH.

Each of the Fmoc amino acids was dissolved in a 0.3 N solution of HOBt in DMF wherein the concentration of the resulting Fmoc amino acid was 0.3 N. A four fold excess (0.27 mmol, 0.9 mL of the 0.3 N solution) of Fmoc amino acid was used for each coupling. DIC (0.27 mmol, 0.6 mL of 0.45N DIC solution in DMF) was used as the coupling reagent for each coupling. Deprotection was performed by using 20% piperidine in DMF (2×1.5 mL per residue).

The peptides were cleaved from the resin by treating the peptide-resins with 8% triisopropylsilane (TIP) in trifluoroacetic acid (TFA) (1.5 mL per reaction well) at room temperature for 2 h. The resin was removed by filtration. Each filtrate was diluted to 25 mL with ether in a centrifuge tube. The resulting precipitate in each tube was centrifuged and the solvents were decanted from the precipitate. The precipitate in each tube was then dissolved in methanol (3 mL) and diluted with water (1 mL). The purification of the crude products was done on a reverse-phase preparative HPLC using a column (100×21.20 mm, 5μ) of LUNA 5μ C8(2) (Phenomenex, Torrance, Calif.). For each peptide, the column was eluted with a linear gradient from 85% A and 15% B to 25% A and 75% B in 15 min with a flow rate of 25 mL/min. A was 0.1% TFA in water and B was 0.1% TFA in acetonitrile/water (80/20, v/v). The fractions were checked by analytical HPLC and those containing the pure product were combined and lyophilized to dryness.

Yields ranged from 13% to 71% and purity of each of Examples 1-65 exceeded 94% based upon analytical HPLC analysis. Electro-spray ionization mass spectrometry (ES-MS) analysis was performed and observed molecular weights were in agreement with calculated molecular weights. The results are detailed in Table I, below.

Examples 66-69

Examples 66-69 were synthesized according to the following procedure.

1.a. BOC-(D)-Trp-OH (4.0 g, 13.1 mmole) (Novabiochem San Diego, Calif.) in methanol (36 ml) and $Cs_2CO_3$ (2.14 g, 6.57 mmole) in water (10 ml) were combined and the mixture was swirled until a homogeneous mixture was obtained. Solvents were removed in vacuo and the residue was dissolved in DMF (45 ml). 2-bromoacetophenone (2.61 g, 13.1 mmole) in DMF (9 ml) was added to the solution and the solution was stirred for 30 min. at room temperature. Cesium bromide was removed by filtration and the filtrate was concentrated in vacuo. The resulting concentrate was dissolved in xylenes (45 ml), $NH_4OAc$ (17.1 g) was added, and the solution was heated at reflux for 1 hr. The cooled solution was washed two times with saturated $NaHCO_3$ solution (45 ml) and then with saturated NaCl. The resulting organic layer was purified by flash chromatography to yield 4.1 g (77%) of intermediate 1A depicted in Scheme 1A, ("Compound 1A").

Scheme 1A

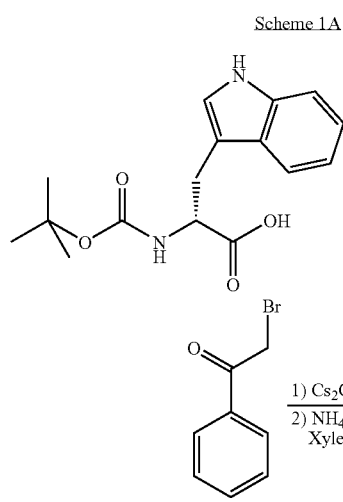

1b. Compound 1A (403 mg) was deblocked using a mixture of trifluoroacetic acid (TFA) (8 ml) dichloromethane (DCM) (8 ml) and triisopropylsilane (TIPS) (1.4 ml). After mixing for one hour the solution was concentrated under a stream of nitrogen. The residue was dissolved in DCM (40 ml), washed two times with a saturated solution of NaHCO₃ (40 ml), and then dried over Na₂SO₄ to yield a solution of the intermediate product 1B, depicted in Scheme 1B, below.

Scheme 1B

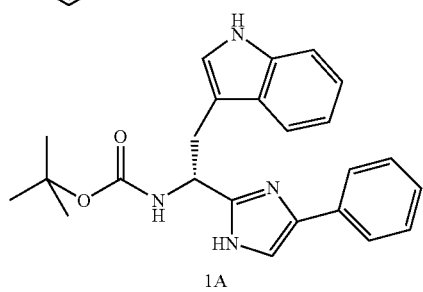

1c.-f. The forgoing solution of the intermediate product 1B was divided into four equal portions and coupled with the pre-activated HOBT esters of FMOC protected amino acids, as summarized in reaction schemes 1C, 1D, 1E, and 1F, below. The amino acid used for each of example 66, 67, 68 and 69 was as follows:

Ex. 66: FMOC-D-2Nal-OH (130 mg, 0.30 mmole) (Synthetech Albany, Oreg.)

Ex. 67: FMOC-D-1Nal-OH (130 mg, 0.30 mmole) (Advanced Chemtech Louisville, Ky.)

Ex. 68: FMOC-D-Bal-OH (132 mg, 0.30 mmole) (Chem Impex Wood Dale, Ill.)

Ex. 69: FMOC-DSer(Bzl)-OH (124 mg, 0.30 mmole) (Chem Impex Wood Dale, Ill.)

Each of the immediately foregoing amino acids was pre-activated with HOBT (46 mg, 0.30 mmole) and DIC (38 mg, 0.30 mmole) in DCM (5 ml) for ten minutes before addition to one of the four portions of the forgoing solution of the intermediate product 1B. The coupling reaction was then allowed to proceed for 30 minutes at room temperature.

Scheme 1C

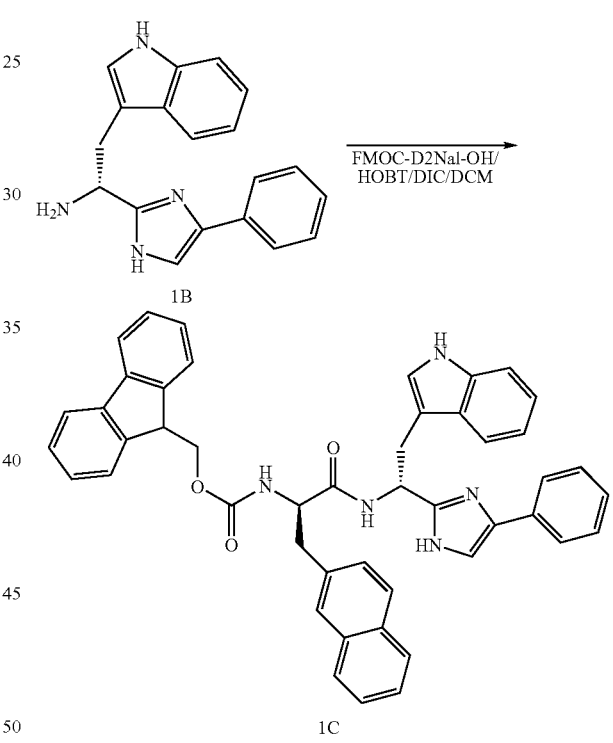

Scheme 1D

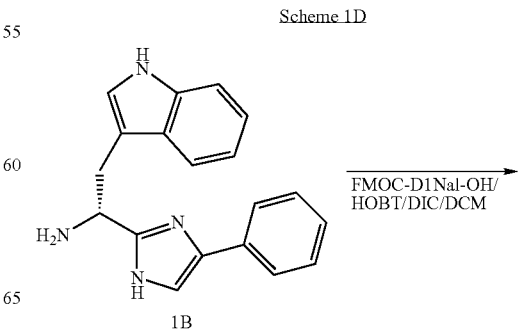

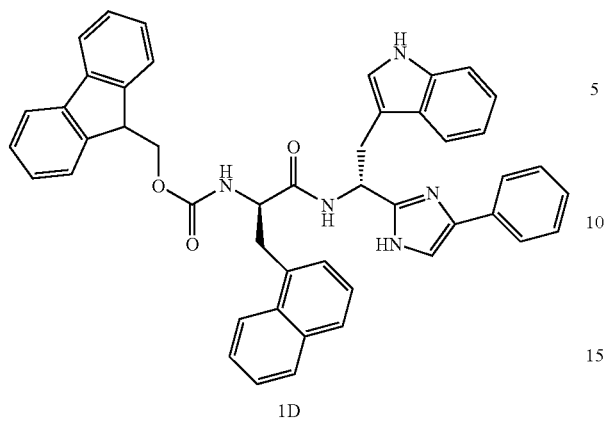

1D

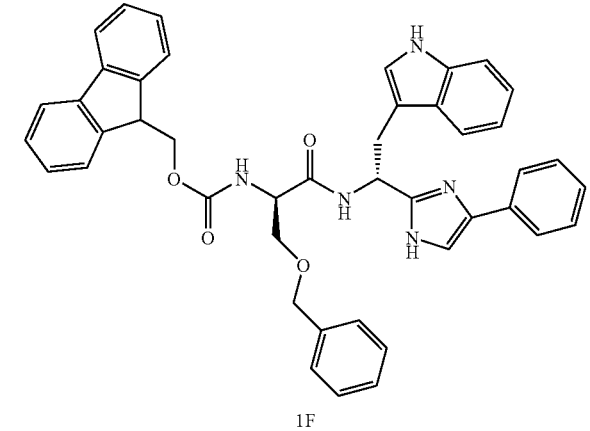

1F 1.g-j. The FMOC group is removed from each of the resulting compounds 1C, 1D, 1E and 1F by addition of tris(2-aminoethyl)amine (0.9 ml) to the respective reaction mixtures from the previous step and mixing for 30 minutes at room temperature. The reaction mixtures containing the deblocked compounds were then washed three times with 10% pH 5.5 phosphate buffer (10 ml).

The resulting free amine solutions were coupled with pre-activated HOBT esters of FMOC or BOC protected aminoacids, as follows:

Ex. 66: FMOC-Inp-OH (105 mg, 0.30 mmole) (Chem Impex Wood Dale, Ill.)

Ex. 67: FMOC-Inp-OH (105 mg, 0.30 mmole)

Ex. 68: BOC-Inp-OH (68.3 mg, 0.30 mmole) (Bachem Torrance, Calif.

Ex. 69: BOC-Aib-OH (60.6 mg, 0.30 mmole) (Bachem Torrance, Calif.)

Each of the immediately foregoing amino acids was pre-activated with HOBT (46 mg, 0.30 mmole) and DIC (38 mg, 0.30 mmole) in DCM (5 ml) for ten minutes before addition to the appropriate deprotected amine. The coupling reaction was then allowed to proceed for one hour at room temperature.

Deprotection—Compounds 66-67. The FMOC group was removed from the resulting FMOC-protected compounds by addition of tris(2-aminoethyl)amine (0.9 ml) and mixing for 30 minutes. The deblocked compounds were washed three times with 10% pH 5.5 phosphate buffer (10 ml) and the crude products were collected as a precipitate.

Deprotection—Compounds 68-69. The BOC-protected compounds were purified by flash chromatography and then deblocked for one hour with TIPS (0.50 ml), TFA (0.50 ml), in DCM (2.75 ml). The crude products were then concentrated and dried under vacuum.

Purification by HPLC afforded the products in 5% and 29% yields for the compounds of examples 66 and 67, respectively, and 15% and 43% for the compounds of examples 68 and 69, respectively.

The foregoing deprotection, coupling, and deprotection steps are summarized in reaction schemes 1G, 1H, 1I and 1J, below Scheme 1E

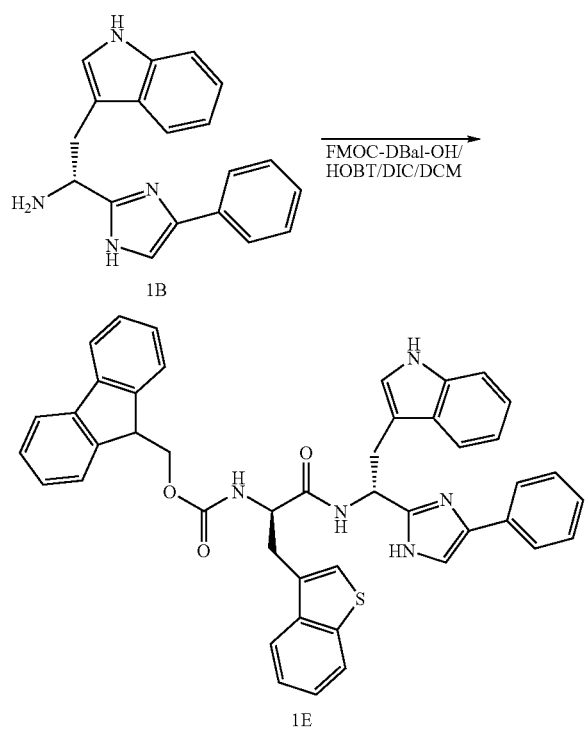

Scheme 1F

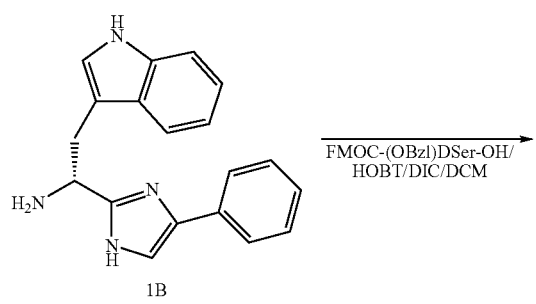

Scheme 1G
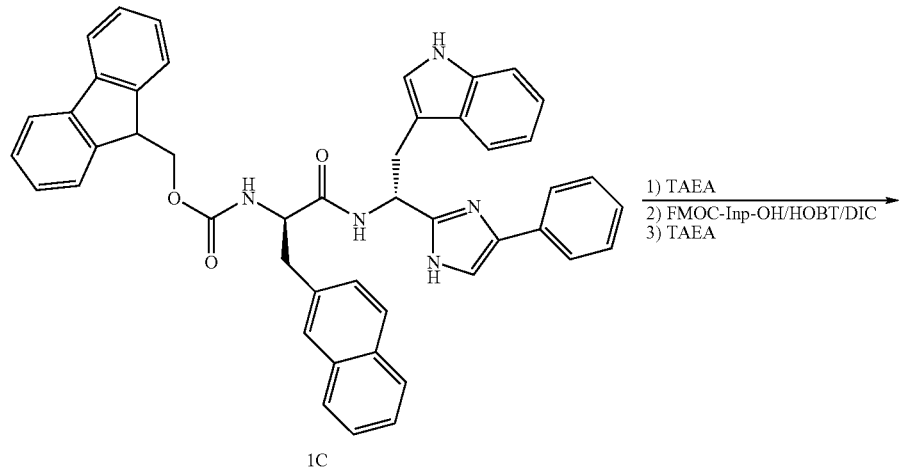
1C
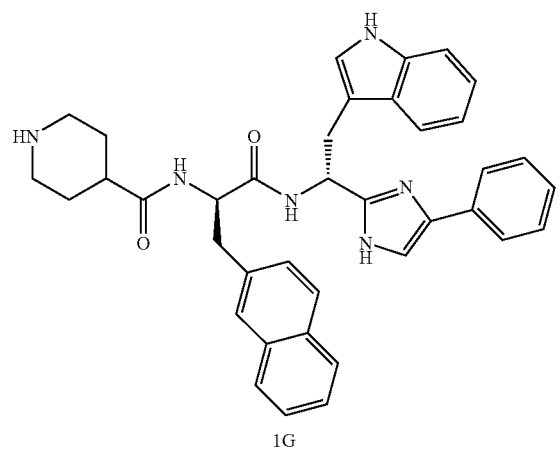
1G
Scheme 1H
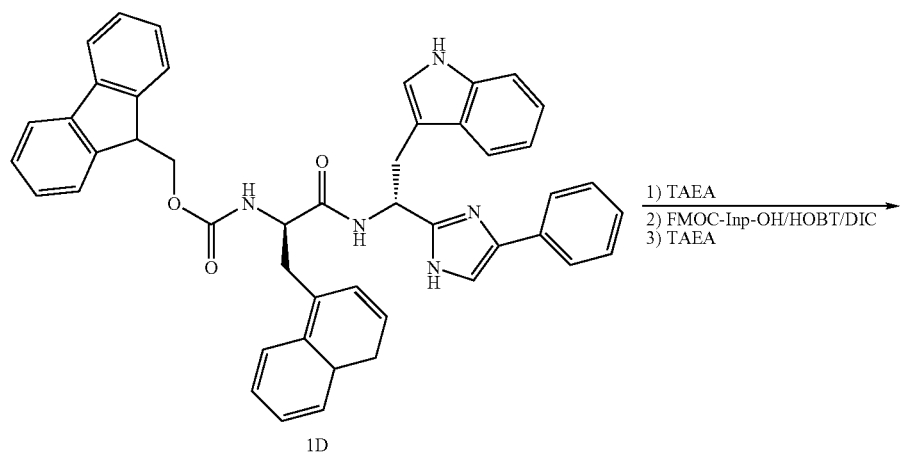
1D

-continued
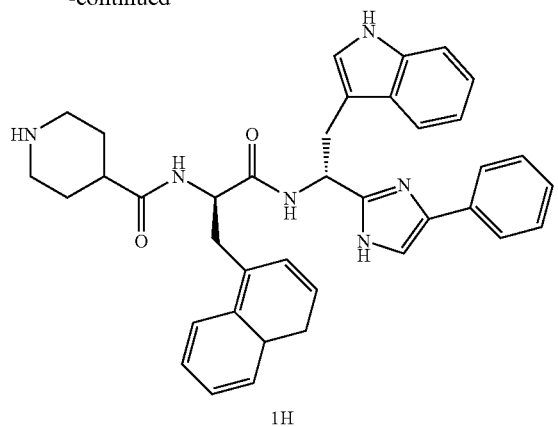
1H
Scheme 1I
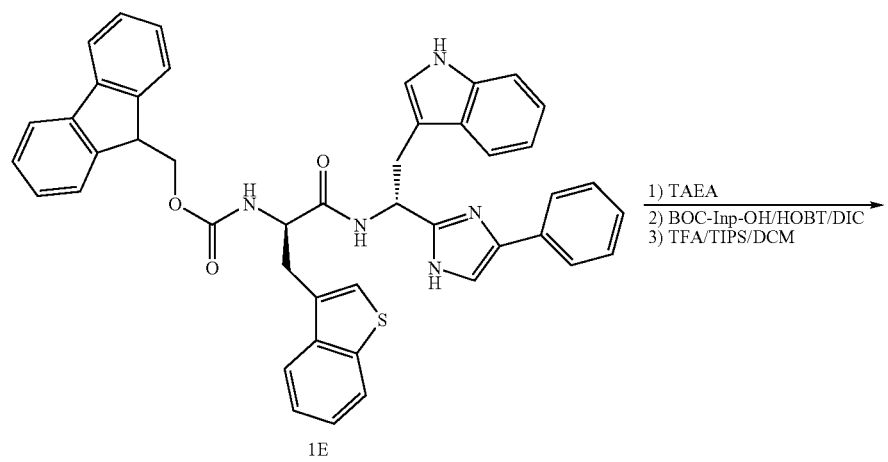
1E
1) TAEA
2) BOC-Inp-OH/HOBT/DIC
3) TFA/TIPS/DCM
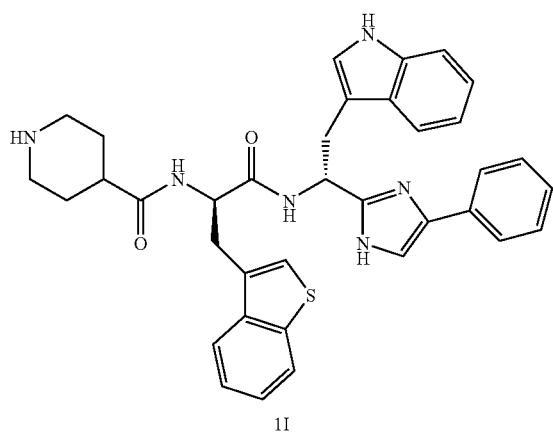
1I

Scheme 1J

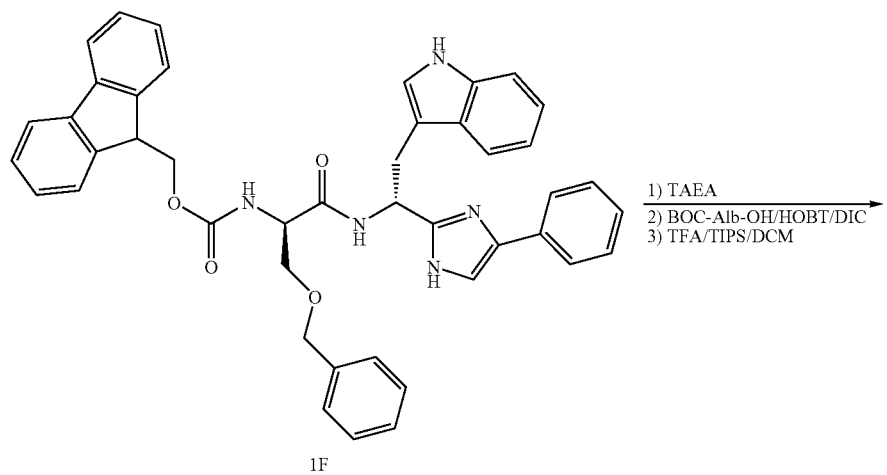

Example 70

H-Inp-D-Trp-2Nal(Ψ)-Pim

Compound 70 was synthesized according to the following procedure.

2.a.1 and 2.a.2.: Compound 2A was made in an analogous manner as was Compound 1A, using BOC-D-2Nal-OH and 2-bromoacetophenone as starting materials.

Steps 2.a.1. and 2.a.2. are summarized in Scheme 2A, below.

Scheme 2A

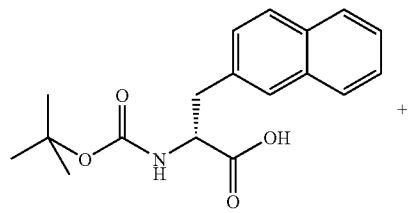

+

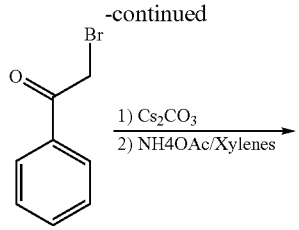

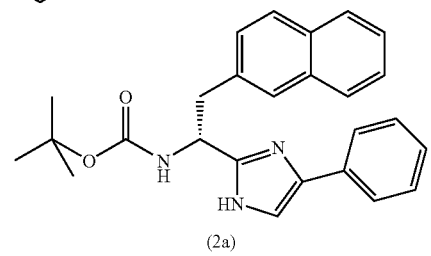

(2a)

2.b.1. Compound 2A (100 mg, 0.242 mmole) was deblocked in TFA (2 ml) and DCM (2 ml) for one hour. Volatiles were then removed under a stream of nitrogen and the residue was dissolved in DCM (10 ml). The resulting solution washed three times with saturated NaHCO₃ (10 ml) to yield a solution of Compound 2A in free amine form.

2.b.2. The active ester of FMOC-D-Trp-(BOC)—OH (153 mg, 0.290 mmole) was preformed with N-hydroxysuccinimide (HOSu; 33 mg, 0.290 mmole) and DIC (37 mg, 0.290 mmole) in DCM (1.5 ml). After one hour diisopropylurea was removed by filtration and the filtrate was added to the Compound 2A (free amine) solution. The resulting solution was diluted with DCM to 4 ml and the coupling reaction allowed to proceed for 30 minutes.

Steps 2.b.1. and 2.b.2. are summarized in Scheme 2B, below.

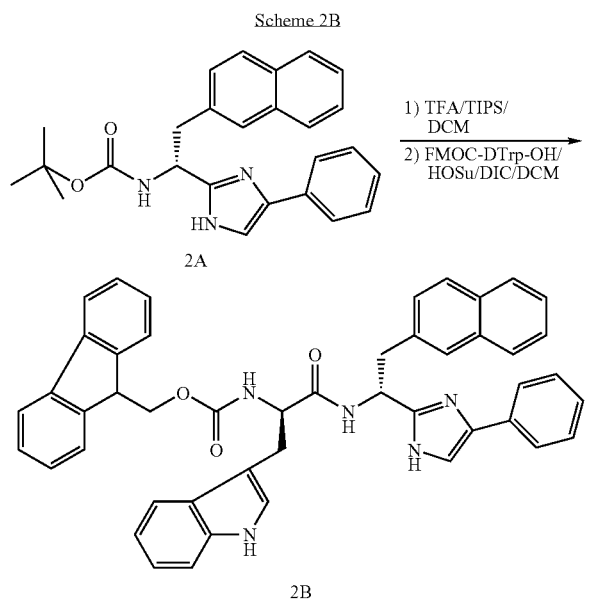

Scheme 2B 2.c.1 Compound 2B was deblocked by addition of tris(2-aminoethyl)amine (TAEA) (0.9 ml) to the immediately foregoing coupling reaction solution and mixing for 30 minutes at room temperature. The reaction solution was then washed three times with saturated NaCl solution (10 ml) followed by three times with 10% pH 5.5 phosphate buffer (10 ml) to yield a solution of Compound 2B in free amine form.

2.c.2. The active ester of BOC-Inp-OH (66.5 mg, 0.290 mmole) was preformed with HOSu (33 mg, 0.290 mmole) and DIC (37 mg 0.290 mmole) in DCM (1.5 ml). After one hour diisopropylurea was removed by filtration and the filtrate was added to the Compound 2B (free amine) solution. The resulting solution was diluted with DCM to 4 ml and the coupling reaction was allowed to proceed for 12 hours.

The reaction mixture was then washed three times with 10% pH 5.5 phosphate buffer (10 ml) and dried over $Na_2SO_4$. Solvent was removed under vacuum and the concentrate was purified by flash chromatography.

2.c.3. The intermediate was deblocked using TFA (2.75 ml) and TIPS (0.5 ml) in DCM (2.75 ml) for 30 minutes. Volatiles were removed from the reaction mixture under a stream of nitrogen and the residue was triturated with ether (15 ml). After centrifugation the ether was decanted and the resulting solid was subjected to HPLC to yield purified Compound 70 in 39% yield.

Steps 2.c.1. and 2.c.2. and 2.c.3. are summarized in Scheme 2C, below.

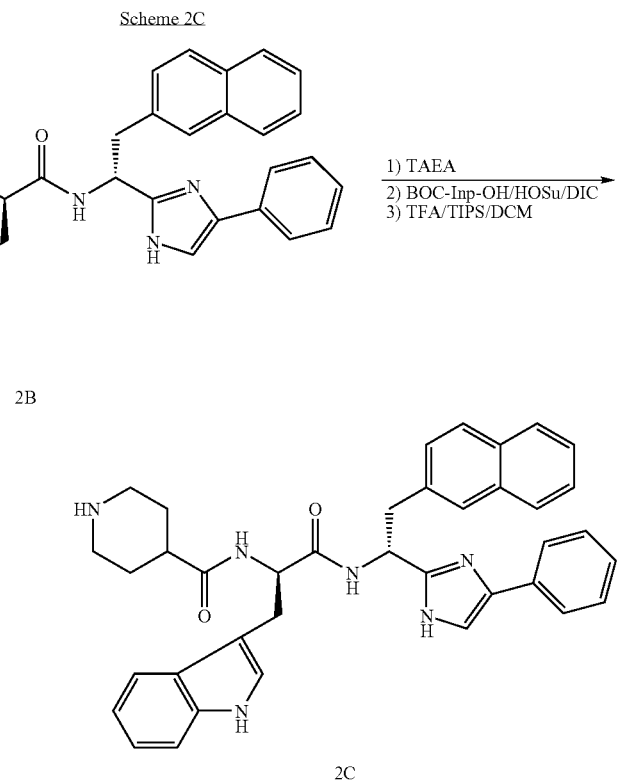

Scheme 2C

Other peptides of the invention can be prepared by a person of ordinary skill in the art using synthetic procedures analogous to those disclosed generally hereinabove and/or to those disclosed specifically in the foregoing examples, as were the compounds depicted in Table 1.

TABLE 1

| Ex. No. | Purity Sequence | Mol. Wt. (Calc.) | Mol. Wt. (MS-ES) | Purity (%) |
|---|---|---|---|---|
| 1 | H-Inp-D-1Nal-D-Trp-3Pal-Lys-NH$_2$ | 787.96 | 787.4 | 96 |
| 2 | H-Inp-D-2Nal-D-Trp-4Pal-Lys-NH$_2$ | 787.96 | 787.4 | 99 |
| 3 | H-Inp-D-2Nal-D-Trp-Orn-Lys-NH$_2$ | 753.94 | 753.4 | 98 |
| 4 | H-Inp-D-Bip-D-Trp-Phe-Lys-NH$_2$ | 813.01 | 812.4 | 99 |
| 5 | H-Inp-D-2Nal-D-Trp-Thr(Bzl)-Lys-NH$_2$ | 831.03 | 830.4 | 98 |
| 6 | H-Inp-D-2Nal-D-Trp-Pff-Lys-NH$_2$ | 876.92 | 876.3 | 98 |
| 7 | H-Inp-D-2Nal-D-Trp-Thi-Lys-NH$_2$ | 793.00 | 792.4 | 98 |
| 8 | H-Inp-D-2Nal-D-Trp-Taz-Lys-NH$_2$ | 793.99 | 793.4 | 97 |
| 9 | H-Inp-D-Dip-D-Trp-Phe-Lys-NH$_2$ | 813.01 | 812.4 | 98 |
| 10 | H-Inp-D-Bpa-D-Trp-Phe-Lys-NH$_2$ | 841.02 | 840.4 | 95 |
| 11 | H-Inp-D-2Nal-D-Bpa-Phe-Lys-NH$_2$ | 852.04 | 851.3 | 99 |
| 12 | H-Inp-D-2Nal-D-Trp-3Pal-NH$_2$ | 659.79 | 659.3 | 99 |
| 13 | H-Inp-D-2Nal-D-Trp-4Pal-NH$_2$ | 659.79 | 659.3 | 98 |
| 14 | H-Inp-D-1Nal-D-Trp-3Pal-NH$_2$ | 659.79 | 659.3 | 98 |
| 15 | H-Inp-D-Bip-D-Trp-Phe-NH$_2$ | 684.84 | 684.3 | 99 |
| 16 | H-Inp-D-2Nal-D-Trp-Thr(Bzl)-NH$_2$ | 702.85 | 702.3 | 99 |
| 17 | H-Inp-D-2Nal-D-Trp-Pff-NH$_2$ | 748.75 | 748.2 | 99 |
| 18 | H-Inp-D-2Nal-D-Trp-2Thi-NH$_2$ | 664.83 | 664.2 | 99 |
| 19 | H-Inp-D-2Nal-D-Trp-Taz-NH$_2$ | 665.82 | 665.3 | 98 |
| 20 | H-Inp-D-Dip-D-Trp-Phe-NH$_2$ | 684.84 | 684.3 | 98 |
| 21 | H-Inp-D-2Nal-D-Dip-Phe-NH$_2$ | 695.86 | 695.3 | 99 |
| 22 | H-Inp-D-Bal-D-Trp-Phe-NH$_2$ | 664.83 | 664.3 | 97 |
| 23 | H-Inp-D-2Nal-D-Bal-Phe-NH$_2$ | 675.85 | 675.2 | 99 |
| 24 | H-Inp-D-2Nal-D-Trp-3Pal-Lys-NH$_2$ | 787.96 | 787.5 | 97 |
| 25 | H-Inp-D-Bal-D-Trp-2Thi-Lys-NH$_2$ | 799.03 | 798.4 | 99 |
| 26 | H-Inp-D-Bal-D-Trp-Phe-Lys-NH$_2$ | 793.00 | 792.4 | 99 |
| 27 | H-Inp-D-1Nal-D-Trp-2Thi-Lys-NH$_2$ | 793.00 | 792.4 | 99 |
| 28 | H-Inp-D-2Nal-D-Trp-Phe-Apc-NH$_2$ | 784.96 | 784.4 | 98 |
| 29 | H-Inp-D-1Nal-D-Trp-Phe-Apc-NH$_2$ | 784.96 | 784.4 | 98 |
| 30 | H-Inp-D-Bal-D-Trp-Phe-Apc-NH$_2$ | 790.99 | 790.4 | 97 |
| 31 | H-Apc-D-2Nal-D-Trp-Phe-Lys-NH$_2$ | 801.99 | 801.4 | 98 |
| 32 | H-Apc-D-1Nal-D-Trp-2Thi-Lys-NH$_2$ | 808.02 | 807.4 | 99 |
| 33 | H-Inp-D-1Nal-D-Trp-2Thi-NH$_2$ | 664.83 | 664.2 | 98 |
| 34 | H-Apc-D-1Nal-D-Trp-Phe-NH$_2$ | 673.81 | 673.3 | 99 |
| 35 | H-Inp-D-1Nal-D-Trp-Taz-Lys-NH$_2$ | 793.99 | 793.5 | 99 |
| 36 | H-Inp-D-Bal-D-Trp-Taz-Lys-NH$_2$ | 800.02 | 799.4 | 99 |
| 37 | H-Apc-D-1Nal-D-Trp-Taz-Lys-NH$_2$ | 809.00 | 808.5 | 99 |
| 38 | H-Apc-D-Bal-D-Trp-Taz-Lys-NH$_2$ | 815.03 | 814.4 | 99 |
| 39 | H-Apc-D-Bal-D-Trp-2Thi-Lys-NH$_2$ | 814.04 | 813.4 | 98 |
| 40 | H-Inp-D-1Nal-D-Trp-2Thi-Apc-NH$_2$ | 790.99 | 790.5 | 97 |
| 41 | H-Inp-D-Bal-D-Trp-2Thi-Apc-NH$_2$ | 797.01 | 796.4 | 97 |
| 42 | H-Apc-D-1Nal-D-Trp-2Thi-Apc-NH$_2$ | 806.00 | 805.5 | 97 |
| 43 | H-Apc-D-Bal-D-Trp-2Thi-Apc-NH$_2$ | 812.03 | 811.4 | 98 |
| 44 | H-Apc-D-1Nal-D-Trp-Phe-Lys-NH$_2$ | 801.99 | 801.5 | 98 |
| 45 | H-Apc-D-Bal-D-Trp-Phe-Lys-NH$_2$ | 808.02 | 807.5 | 99 |
| 46 | H-Apc-D-1Nal-D-Trp-Phe-Apc-NH$_2$ | 799.97 | 799.5 | 98 |
| 47 | H-Apc-D-Bal-D-Trp-Phe-Apc-NH$_2$ | 806.00 | 805.5 | 98 |
| 48 | H-Apc-D-1Nal-D-1Nal-Phe-Apc-NH$_2$ | 811.00 | 810.5 | 95 |
| 49 | H-Apc-D-1Nal-D-2Nal-Phe-Apc-NH$_2$ | 811.00 | 810.5 | 96 |
| 50 | H-Apc-D-1Nal-D-1Nal-Phe-Lys-NH$_2$ | 813.01 | 812.5 | 99 |
| 51 | H-Apc-D-Bal-D-1Nal-Phe-Apc-NH$_2$ | 817.02 | 816.5 | 96 |
| 52 | H-Apc-D-Bal-D-2Nal-Phe-Apc-NH$_2$ | 817.02 | 816.5 | 94 |
| 53 | H-Apc-D-Bal-D-1Nal-Phe-Lys-NH$_2$ | 819.04 | 818.5 | 99 |
| 54 | H-Apc-D-Bal-D-2Nal-Phe-Lys-NH$_2$ | 819.04 | 818.5 | 98 |
| 55 | H-Apc-D-1Nal-D-Trp-2Thi-NH$_2$ | 679.84 | 679.2 | 98 |
| 56 | H-Apc-D-Bal-D-Trp-Phe-NH$_2$ | 679.84 | 679.3 | 99 |
| 57 | H-Apc-D-1Nal-D-Trp-Taz-NH$_2$ | 680.83 | 680.3 | 99 |
| 58 | H-Apc-D-Bal-D-Trp-2Thi-NH$_2$ | 685.87 | 685.2 | 97 |
| 59 | H-Apc-D-Bal-D-Trp-Taz-NH$_2$ | 686.86 | 686.2 | 99 |
| 60 | H-Apc-D-2Nal-D-Trp-2Thi-NH$_2$ | 679.84 | 679.2 | 95 |
| 61 | H-Apc-D-2Nal-D-Trp-Taz-NH$_2$ | 680.83 | 680.2 | 97 |
| 62 | H-Inp-D-1Nal-D-Trp-Taz-Apc-NH$_2$ | 791.97 | 791.5 | 98 |
| 63 | H-Inp-D-Bal-D-Trp-Taz-Apc-NH$_2$ | 798.00 | 797.4 | 99 |
| 64 | H-Apc-D-1Nal-D-Trp-Taz-Apc-NH$_2$ | 806.99 | 806.5 | 99 |
| 65 | H-Apc-D-Bal-D-Trp-Taz-Apc-NH$_2$ | 813.02 | 812.4 | 98 |
| 66 | H-Inp-D-2Nal-D-Trp($\psi$)-Pim | 610.77 | 611.4 | 99 |
| 67 | H-Inp-D-1Nal-D-Trp($\psi$)-Pim | 610.77 | 611.3 | 99 |
| 68 | H-Inp-D-Bal-D-Trp($\psi$)-Pim | 616.79 | 617.3 | 99 |
| 69 | H-Aib-D-Ser(Bzl)-D-Trp($\psi$)-Pim | 564.69 | 565.3 | 99 |
| 70 | H-Inp-D-Trp-D-2Nal($\psi$)-Pim | 610.77 | 611.4 | 99 |

Biological Assay

The activities of compounds of the invention at the GHS receptor can be and were determined using techniques such as those described in the examples provided below. In different embodiments a ghrelin analog has at least about 50%, at least about 60%, at least about 70%, at least about 80%, or at least about 90%, functional activity relative to ghrelin as determined using one or more of the Functional Activity assays described below; and/or has an $IC_{50}$ greater than about 1,000 nM, greater than about 100 nM, or greater than about 50 nM, using the Receptor Binding assay described below. With respect to $IC_{50}$, greater refers to potency and thus indicates a lesser amount is needed to achieve binding inhibition.

Assays measuring the ability of a compound to bind a GHS receptor employ a GHS receptor, a fragment of the receptor comprising a ghrelin binding site, a polypeptide comprising such a fragment, or a derivative of the polypeptide. Preferably, the assay uses the GHS receptor or a fragment thereof. A polypeptide comprising a GHS receptor fragment that binds ghrelin can also contain one or more polypeptide regions not found in a GHS receptor. A derivative of such a polypeptide comprises a GHS receptor fragment that binds ghrelin along with one or more non-peptide components.

The GHS receptor amino acid sequence involved in binding can be readily identified using labeled ghrelin or ghrelin structural or functional analogs and different receptor fragments. Different strategies can be employed to select fragments to be tested to narrow down the binding region. Examples of such strategies include testing consecutive fragments about 15 amino acids in length starting at the N-terminus, and testing longer length fragments. If longer length fragments are tested, a fragment binding ghrelin can be subdivided to further locate the ghrelin binding region. Fragments used for binding studies can be generated using recombinant nucleic acid techniques.

Binding assays can be performed using individual compounds or preparations containing different numbers of compounds. A preparation containing different numbers of compounds having the ability to bind to the GHS receptor can be divided into smaller groups of compounds that can be tested to identify the compound(s) binding to the GHS receptor. In an embodiment of the present invention, a test preparation containing at least 10 compounds is used in a binding assay.

Binding assays can be performed using recombinantly produced GHS receptor polypeptides present in different environments. Such environments include, for example, cell extracts and purified cell extracts containing the GHS receptor polypeptide expressed from recombinant nucleic acid or naturally occurring nucleic acid; and also include, for example, the use of a purified GHS receptor polypeptide produced by recombinant means or from naturally occurring nucleic acid which is introduced into a different environment.

Screening for GHS Receptor Active Compounds

Screening for GHS receptor active compounds is facilitated using a recombinantly expressed receptor. Using a recombinantly expressed GHS receptor offers several advantages such as the ability to express the receptor in a defined cell system so that a response to a compound at the GHS receptor can more readily be differentiated from responses at other receptors. For example, the GHS receptor can be expressed in a cell line such as HEK 293, COS 7, and CHO not normally expressing the receptor by an expression vector, wherein the same cell line without the expression vector can act as a control.

Screening for compounds reducing GHS receptor activity is facilitated through the use of a ghrelin functional analog in the assay. The use of a ghrelin functional analog in a screening assay provides for GHS receptor activity. The effect of test compounds on such activity can be measured to identify, for example, allosteric modulators and antagonists.

GHS receptor activity can be measured using different techniques such as detecting a change in the intracellular conformation of the GHS receptor, in the G-protein coupled activities, and/or in the intracellular messengers. Preferably, GHS receptor activity is measured using techniques such as those measuring intracellular $Ca^{2+}$. Examples of techniques well known in the art that can be employed to measure $Ca^{2+}$ include the use of dyes such as Fura-2 and the use of $Ca^{2+}$-bioluminescent sensitive reporter proteins such as aequorin. An example of a cell line employing aequorin to measure G-protein activity is HEK293/aeq17. (Button et al., 1993. Cell Calcium 14, 663-671, and Feighner et al., 1999, Science 284, 2184-2188.)

Chimeric receptors containing a ghrelin binding region functionally coupled to a different G-protein can also be used to measure GHS receptor activity. A chimeric GHS receptor contains an N-terminal extracellular domain; a transmembrane domain made up of transmembrane regions, extracellular loop regions, and intracellular loop regions; and an intracellular carboxy terminus. Techniques for producing chimeric receptors and measuring G-protein coupled responses are provided in, for example, International Application Number WO 97/05252, and U.S. Pat. No. 5,264,565, both of which are hereby incorporated by reference herein.

Stimulation of GHS Receptor Activity

Structural and/or functional analogs of ghrelin can be used to stimulate GHS receptor activity. Such stimulation can be used, for example, to study the effect of GHS receptor modulation, to study the effect of growth hormone secretion, to look for or study ghrelin antagonists, or to achieve a beneficial effect in a subject. Beneficial effects that can be achieved include one or more of the following: treating a growth hormone deficient state, increasing muscle mass, increasing bone density, treating sexual dysfunction in males or females, facilitating a weight gain, facilitating maintenance of weight, facilitating maintenance of physical functioning, facilitating recovery of physical function, and/or facilitating appetite increase.

Increasing weight or appetite can be useful for maintaining weight or producing a weight or appetite gain in an under weight subject, or in a patient having a disease or undergoing treatment that affects weight or appetite. In addition, for example, farm animals such as pigs, cows and chickens can be treated to gain weight.

Underweight subjects include those having a body weight about 10% or less, 20% or less, or 30% or less, than the lower end of a "normal" weight range or Body Mass Index ("BMI"). BMI measures a subject's height/weight ratio and is determined by calculating weight in kilograms divided by the square of height in meters. BMI measures your height/weight ratio. It is determined by calculating weight in kilograms divided by the square of height in meters. The BMI "normal" range for humans is generally considered to be 19-22. "Normal" weight ranges are well known in the art and take into account factors such as a subject age, height, and body type.

Biological Assays

Examples

1. Receptor Binding Assay

A. Preparation of CHO-K1 Cells Expressing the Human Recombinant GHS Receptor

The cDNA for human growth hormone secretagogue receptor (hGHS-R, or ghrelin receptor) was cloned by Polymerase Chain Reaction (PCR) using human brain RNA as a template (Clontech, Palo Alto, Calif.), gene specific primers flanking the full-length coding sequence of hGHS-R, (S: 5'-A T G T G G A A C G C G A C G C C C A G C G A A G A G-3'

(SEQ ID NO:1) and AS: 5'-T C A T G T A T T A A T A C T A G A T T C T G T C C A-3') (SEQ ID NO:2), and Advantage 2 PCR Kit (Clontech). The PCR product was cloned into the pCR2.1 vector using Original TA Cloning Kit (Invitrogen, Carlsbad, Calif.). The full length human GHS-R was subcloned into the mammalian expression vector pcDNA 3.1 (Invitrogen). The plasmid was transfected into the Chinese hamster ovary cell line, CHO-K1 (American Type Culture Collection, Rockville, Md.), by calcium phosphate method (Wigler, M et al., Cell 11, 223, 1977). Single cell clones stably expressing the hGHS-R were obtained by selecting transfected cells grown in cloning rings in RPMI 1640 media supplemented with 10% fetal bovine serum and 1 mM sodium pyruvate containing 0.8 mg/ml G418 (Gibco, Grand Island, N.Y.).

B. GHS-R Binding Assay:

Membranes for radioligand binding studies can be and were prepared by homogenization of the foregoing CHO-K1 cells expressing the human recombinant GHS receptor in 20 ml of ice-cold 50 mM Tris-HCl with a Brinkman Polytron (Westbury, N.Y.) (setting 6, 15 sec). The homogenates were washed twice by centrifugation (39,000 g 10 min), and the final pellets were resuspended in 50 mM Tris-HCl, containing 2.5 mM $MgCl_2$, and 0.1% BSA. For assay, aliquots (0.4 ml) were incubated with 0.05 nM ($^{125}$I)ghrelin (~2000 Ci/mmol, Perkin Elmer Life Sciences, Boston, Mass.), with and without 0.05 ml of unlabeled competing test compounds of the invention. After a 60 min incubation (4° C.), the bound ($^{125}$I) ghrelin was separated from the free by rapid filtration through GF/C filters (Brandel, Gaithersburg, Md.), which had been previously soaked in 0.5% polyethyleneimine/0.1% BSA. The filters were then washed three times with 5-ml aliquots of ice-cold 50 mM Tris-HCl and 0.1% bovine serum albumin, and the bound radioactivity trapped on the filters was counted by gamma spectrometry (Wallac LKB, Gaithersburg, Md.). Specific binding was defined as the total ($^{125}$I)ghrelin bound minus that bound in the presence of 1000 nM ghrelin (Bachem, Torrence, Calif.).

2. GHS-R Functional Activity Assays

A. In Vitro GSH Receptor Mediated Intracellular $iCa^{2+}$ Mobilization

The foregoing CHO-K1 cells expressing the human GSH receptor were harvested by incubating in a 0.3% EDTA/phosphate buffered saline solution (25° C.), and washed twice by centrifugation. The washed cells were resuspended in Hank's-buffered saline solution (HBSS) for loading of the fluorescent $Ca^{2+}$ indicator Fura-2AM. Cell suspensions of approximately $10^8$ cells/ml were incubated with 2 µM Fura-2AM for 30 min at about 25° C. Unloaded Fura-2AM was removed by centrifugation twice in HBBS, and the final suspensions were transferred to a spectrofluorometer (Hitachi F-2000) equipped with a magnetic stirring mechanism and a temperature-regulated cuvette holder. After equilibration to 37° C., the compounds of the invention were added for measurement of intracellular $Ca^{2+}$ mobilization. The excitation and emission wavelengths were 340 and 510 nm, respectively.

B. In Vivo GH Release/Suppression

As is well known in the art, compounds may be tested for their ability to stimulate or suppress release of growth hormone (GH) in vivo. (See, e.g., Deghenghi, R., et al., Life Sciences 54, 1321-1328 (1994); International Application No. WO 02/08250.) Thus for example in order to ascertain a compound's ability to stimulate GH release in vivo the compound may be injected subcutaneously in 10-day old rats at a dose of, e.g., 300 mg/kg. The circulating GH may be determined at, e.g., 15 minutes after injection and compared to GH levels in rats injected with a solvent control.

Similarly, compounds may be tested for their ability to antagonize ghrelin-induced GH secretion in vivo. Thus a compound may be injected subcutaneously in 10-day old rats at a dose of, e.g., 300 mg/kg, along with ghrelin. Again the circulating GH may be determined at, e.g., 15 minutes after injection and compared to GH levels in rats injected with ghrelin alone.

Administration

The compounds of the invention can be formulated and administered to a subject using the guidance provided herein along with techniques well known in the art. The preferred route of administration ensures that an effective amount of compound reaches the target. Guidelines for pharmaceutical administration in general are provided in, for example, *Remington's Pharmaceutical Sciences* 18$^{th}$ Edition, Ed. Gennaro, Mack Publishing, 1990, and *Modem Pharmaceutics* 2$^{nd}$ Edition, Eds. Banker and Rhodes, Marcel Dekker, Inc., 1990, both of which are hereby incorporated by reference herein.

The compounds of the invention can be prepared as acidic or basic salts. Pharmaceutically acceptable salts (in the form of water- or oil-soluble or dispersible products) include conventional non-toxic salts or the quaternary ammonium salts that are formed, e.g., from inorganic or organic acids or bases. Examples of such salts include acid addition salts such as acetate, adipate, alginate, aspartate, benzoate, benzenesulfonate, bisulfate, butyrate, citrate, camphorate, camphorsulfonate, cyclopentanepropionate, digluconate, dodecylsulfate, ethanesulfonate, fumarate, glucoheptanoate, glycerophosphate, hemisulfate, heptanoate, hexanoate, hydrochloride, hydrobromide, hydroiodide, 2-hydroxyethanesulfonate, lactate, maleate, methanesulfonate, 2-naphthalenesulfonate, nicotinate, oxalate, pamoate, pectinate, persulfate, 3-phenylpropionate, picrate, pivalate, propionate, succinate, tartrate, thiocyanate, tosylate, and undecanoate; and base salts such as ammonium salts, alkali metal salts such as sodium and potassium salts, alkaline earth metal salts such as calcium and magnesium salts, salts with organic bases such as dicyclohexylamine salts, N-methyl-D-glucamine, and salts with amino acids such as arginine and lysine.

The compounds of the invention can be administered using different routes including oral, nasal, by injection, transdermal, and transmucosally. Active ingredients to be administered orally as a suspension can be prepared according to techniques well known in the art of pharmaceutical formulation and may contain microcrystalline cellulose for imparting bulk, alginic acid or sodium alginate as a suspending agent, methylcellulose as a viscosity enhancer, and sweeteners/flavoring agents. As immediate release tablets, these compositions may contain microcrystalline cellulose, dicalcium phosphate, starch, magnesium stearate and lactose and/or other excipients, binders, extenders, disintegrants, diluents and lubricants.

Administered by nasal aerosol or inhalation formulations may be prepared, for example, as solutions in saline, employing benzyl alcohol or other suitable preservatives, absorption promoters to enhance bioavailability, employing fluorocarbons, and/or employing other solubilizing or dispersing agents.

The compounds of the invention may also be administered in intravenous (both bolus and infusion), intraperitoneal, subcutaneous, topical with or without occlusion, or intramuscular form. When administered by injection, the injectable solution or suspension may be formulated using suitable non-toxic, parenterally-acceptable diluents or solvents, such as Ringer's solution or isotonic sodium chloride solution, or suitable dispersing or wetting and suspending agents, such as sterile, bland, fixed oils, including synthetic mono- or diglycerides, and fatty acids, including oleic acid.

Suitable dosing regimens are preferably determined taking into account factors well known in the art including type of subject being dosed; age, weight, sex and medical condition of the subject; the route of administration; the renal and hepatic function of the subject; the desired effect; and the particular compound employed.

Optimal precision in achieving concentrations of drug within the range that yields efficacy without toxicity requires a regimen based on the kinetics of the drug's availability to target sites. This Involves a consideration of the distribution, equilibrium, and elimination of a drug. The daily dose for a subject is expected to be between 0.01 and 1,000 mg per subject per day.

The compounds of the invention can be provided in a kit. Such a kit typically contains an active compound in dosage forms for administration. A dosage form contains a sufficient amount of active compound such that a desirable effect can be obtained when administered to a subject during regular intervals, such as 1 to 6 times a day, during the course of 1 or more days. Preferably, a kit contains instructions indicating the use of the dosage form to achieve a desirable affect and the amount of dosage form to be taken over a specified time period.

The invention has been described in an illustrative manner, and it is to be understood that the terminology which has been used is intended to be in the nature of words of description rather than of limitation. Obviously, many modifications and variations of the present invention are possible in light of the above teachings. It is, therefore, to be understood that within the scope of the appended claims the invention may be practiced otherwise than as specifically described.

The patent and scientific literature referred to herein represents knowledge that is available to those with skill in the art. All patents, patent publications and other publications cited herein are hereby incorporated by reference in their entirety.

Other Embodiments

It is to be understood that while the invention has been described in conjunction with the detailed description thereof, that the foregoing description is intended to illustrate and not limit the scope of the invention, which is defined by the scope of the appended claims. Other aspects, advantages, and modifications are within the claims.

What is claimed is:

1. A compound according to formula (I):

$$R^1\text{-}A^1\text{-}A^2\text{-}A^3\text{-}A^4\text{-}A^5\text{-}R^2 \quad (I)$$

or a pharmaceutically acceptable salt thereof, wherein:
  $A^1$ is Inp;
  $A^2$ is D-Bal, D-Bip, D-Bpa, D-Dip, D-1Nal, D-2Nal, D-Ser(Bzl), or D-Trp;
  $A^3$ is D-Bal or D-Trp;
  $A^4$ is 2Fua, Orn, 2 Pal, 3 Pal, 4 Pal, Pff, Phe, Pim, Taz, 2Thi, 3Thi, or Thr(Bzl);
  $A^5$ is Apc or Lys;
  $R^1$ is hydrogen, $(C_{1-6})$alkyl, $(C_{5-14})$aryl, $(C_{1-6})$alkyl$(C_{5-14})$aryl, $(C_{3-8})$cycloakyl, or $(C_{2-10})$acyl; and
  $R^2$ is OH or $NH_2$;
provided that:
  when $A^5$ is Lys, then:
    $A^2$ is D-Bip, D-Bpa, D-Dip or D-Bal; or
    $A^3$ is D-Bal; or
    $A^4$ is 2Thi, 3Thi, Taz, 2Fua, 2 Pal, 3 Pal, 4 Pal, Orn, Thr(Bzl), or Pff; and
  a compound of formula (I) is not H-Inp-D-Bal-D-Trp-Phe-Apc-$NH_2$.

2. A compound according to claim 1, wherein said compound is according to the formula:
  H-Inp-D-1Nal-D-Trp-3 Pal-Lys-$NH_2$;
  H-Inp-D-2Nal-D-Trp-4 Pal-Lys-$NH_2$;
  H-Inp-D-2Nal-D-Trp-Orn-Lys-$NH_2$;
  H-Inp-D-Bip-D-Trp-Phe-Lys-$NH_2$;
  H-Inp-D-2Nal-D-Trp-Thr(Bzl)-Lys-$NH_2$;
  H-Inp-D-2Nal-D-Trp-Pff-Lys-$NH_2$;
  H-Inp-D-2Nal-D-Trp-2Thi-Lys-$NH_2$;
  H-Inp-D-2Nal-D-Trp-Taz-Lys-$NH_2$;
  H-Inp-D-Dip-D-Trp-Phe-Lys-$NH_2$;
  H-Inp-D-Bpa-D-Trp-Phe-Lys-$NH_2$;
  H-Inp-D-2Nal-D-Trp-3 Pal-Lys-$NH_2$;
  H-Inp-D-Bal-D-Trp-2Thi-Lys-$NH_2$;
  H-Inp-D-Bal-D-Trp-Phe-Lys-$NH_2$;
  H-Inp-D-1Nal-D-Trp-2Thi-Lys-$NH_2$;
  H-Inp-D-2Nal-D-Trp-Phe-Apc-$NH_2$;
  H-Inp-D-1Nal-D-Trp-Phe-Apc-$NH_2$;
  H-Inp-D-1Nal-D-Trp-Taz-Lys-$NH_2$;
  H-Inp-D-Bal-D-Trp-Taz-Lys-$NH_2$;
  H-Inp-D-1Nal-D-Trp-Taz-Apc-$NH_2$;
  H-Inp-D-Bal-D-Trp-Taz-Apc-$NH_2$;
  H-Inp-D-1Nal-D-Bal-2Fua-Lys-$NH_2$;
  H-Inp-D-1Nal-D-Bal-2Thi-Lys-$NH_2$;
  H-Inp-D-1Nal-D-Bal-3Thi-Lys-$NH_2$;
  H-Inp-D-1Nal-D-Bal-Pff-Lys-$NH_2$;
  H-Inp-D-1Nal-D-Bal-Phe-Lys-$NH_2$;
  H-Inp-D-1Nal-D-Bal-Taz-Lys-$NH_2$;
  H-Inp-D-1Nal-D-Trp-2Fua-Apc-$NH_2$;
  H-Inp-D-1Nal-D-Trp-2Fua-Lys-$NH_2$;
  H-Inp-D-1Nal-D-Trp-3Thi-Apc-$NH_2$;
  H-Inp-D-1Nal-D-Trp-3Thi-Lys-$NH_2$;
  H-Inp-D-1Nal-D-Trp-Pff-Apc-$NH_2$;
  H-Inp-D-1Nal-D-Trp-Pff-Lys-$NH_2$;
  H-Inp-D-2Nal-D-Trp-2Fua-Apc-$NH_2$;
  H-Inp-D-2Nal-D-Trp-2Thi-Apc-$NH_2$;
  H-Inp-D-2Nal-D-Trp-3Thi-Apc-$NH_2$;
  H-Inp-D-2Nal-D-Trp-3Thi-Lys-$NH_2$;
  H-Inp-D-2Nal-D-Trp-Pff-Apc-$NH_2$;
  H-Inp-D-2Nal-D-Trp-Taz-Apc-$NH_2$;
  H-Inp-D-Bal-D-Bal-2Fua-Lys-$NH_2$;
  H-Inp-D-Bal-D-Bal-2Thi-Lys-$NH_2$;
  H-Inp-D-Bal-D-Bal-3Thi-Lys-$NH_2$;
  H-Inp-D-Bal-D-Bal-Pff-Lys-$NH_2$;
  H-Inp-D-Bal-D-Bal-Phe-Lys-$NH_2$;
  H-Inp-D-Bal-D-Bal-Taz-Lys-$NH_2$;
  H-Inp-D-Bal-D-Trp-2Fua-Apc-$NH_2$;
  H-Inp-D-Bal-D-Trp-2Fua-Lys-$NH_2$;
  H-Inp-D-Bal-D-Trp-3Thi-Apc-$NH_2$;
  H-Inp-D-Bal-D-Trp-3Thi-Lys-$NH_2$;
  H-Inp-D-Bal-D-Trp-Pff-Apc-$NH_2$;
  H-Inp-D-Bal-D-Trp-Pff-Lys-$NH_2$;
  H-Inp-D-Bip-D-Bal-2Fua-Lys-$NH_2$;
  H-Inp-D-Bip-D-Bal-2Thi-Lys-$NH_2$;
  H-Inp-D-Bip-D-Bal-3Thi-Lys-$NH_2$;
  H-Inp-D-Bip-D-Bal-Pff-Lys-$NH_2$;
  H-Inp-D-Bip-D-Bal-Taz-Lys-$NH_2$;
  H-Inp-D-Bip-D-Trp-2Fua-Lys-$NH_2$;
  H-Inp-D-Bip-D-Trp-2Thi-Lys-$NH_2$;
  H-Inp-D-Bip-D-Trp-3Thi-Lys-$NH_2$;
  H-Inp-D-Bip-D-Trp-Pff-Lys-$NH_2$; or
  H-Inp-D-Bip-D-Trp-Taz-Lys-$NH_2$;
or a pharmaceutically acceptable salt thereof.

3. A compound according to claim 2, wherein said compound is according to the formula:

H-Inp-D-1Nal-D-Trp-3 Pal-Lys-NH$_2$;
H-Inp-D-2Nal-D-Trp-4 Pal-Lys-NH$_2$;
H-Inp-D-2Nal-D-Trp-Orn-Lys-NH$_2$;
H-Inp-D-Bip-D-Trp-Phe-Lys-NH$_2$;
H-Inp-D-2Nal-D-Trp-Thr(Bzl)-Lys-NH$_2$;
H-Inp-D-2Nal-D-Trp-Pff-Lys-NH$_2$;
H-Inp-D-2Nal-D-Trp-2Thi-Lys-NH$_2$;
H-Inp-D-2Nal-D-Trp-Taz-Lys-NH$_2$;
H-Inp-D-Dip-D-Trp-Phe-Lys-NH$_2$;
H-Inp-D-Bpa-D-Trp-Phe-Lys-NH$_2$;
H-Inp-D-2Nal-D-Trp-3 Pal-Lys-NH$_2$;
H-Inp-D-Bal-D-Trp-2Thi-Lys-NH$_2$;
H-Inp-D-Bal-D-Trp-Phe-Lys-NH$_2$;
H-Inp-D-1Nal-D-Trp-2Thi-Lys-NH$_2$;
H-Inp-D-2Nal-D-Trp-Phe-Apc-NH$_2$;
H-Inp-D-1Nal-D-Trp-Phe-Apc-NH$_2$;
H-Inp-D-1Nal-D-Trp-Taz-Lys-NH$_2$;
H-Inp-D-Bal-D-Trp-Taz-Lys-NH$_2$;
H-Inp-D-1Nal-D-Trp-Taz-Apc-NH$_2$;
H-Inp-D-Bal-D-Trp-Taz-Apc-NH$_2$;
H-Inp-D-2Nal-D-Trp-3Thi-Lys-NH$_2$;
H-Inp-D-Bal-D-Trp-3Thi-Lys-NH$_2$;
H-Inp-D-Bal-D-Trp-2Fua-Lys-NH$_2$;
H-Inp-D-Bal-D-Trp-Pff-Lys-NH$_2$;
H-Inp-D-Bal-D-Trp-3Thi-Apc-NH$_2$;
H-Inp-D-Bal-D-Trp-2Fua-Apc-NH$_2$;
H-Inp-D-Bal-D-Trp-Pff-Apc-NH$_2$;
H-Inp-D-Bal-D-Bal-Phe-Lys-NH$_2$;
H-Inp-D-Bal-D-Bal-2Thi-Lys-NH$_2$;
H-Inp-D-Bal-D-Bal-3Thi-Lys-NH$_2$;
H-Inp-D-Bal-D-Bal-Taz-Lys-NH$_2$;
H-Inp-D-Bal-D-Bal-2Fua-Lys-NH$_2$;
H-Inp-D-Bal-D-Bal-Pff-Lys-NH$_2$;
H-Inp-D-1Nal-D-Trp-3Thi-Lys-NH$_2$;
H-Inp-D-1Nal-D-Trp-2Fua-Lys-NH$_2$;
H-Inp-D-1Nal-D-Trp-Pff-Lys-NH$_2$;
H-Inp-D-1Nal-D-Bal-Phe-Lys-NH$_2$;
H-Inp-D-1Nal-D-Bal-2Thi-Lys-NH$_2$;
H-Inp-D-1Nal-D-Bal-3Thi-Lys-NH$_2$;
H-Inp-D-1Nal-D-Bal-Taz-Lys-NH$_2$;
H-Inp-D-1Nal-D-Bal-2Fua-Lys-NH$_2$;
H-Inp-D-1Nal-D-Bal-Pff-Lys-NH$_2$;
H-Inp-D-2Nal-D-Trp-2Thi-Apc-NH$_2$;
H-Inp-D-2Nal-D-Trp-3Thi-Apc-NH$_2$;
H-Inp-D-2Nal-D-Trp-Taz-Apc-NH$_2$;
H-Inp-D-2Nal-D-Trp-2Fua-Apc-NH$_2$;
H-Inp-D-2Nal-D-Trp-Pff-Apc-NH$_2$;
H-Inp-D-1Nal-D-Trp-3Thi-Apc-NH$_2$;
H-Inp-D-1Nal-D-Trp-2Fua-Apc-NH$_2$;
H-Inp-D-1Nal-D-Trp-Pff-Apc-NH$_2$;
H-Inp-D-Bip-D-Trp-2Thi-Lys-NH$_2$;
H-Inp-D-Bip-D-Trp-3Thi-Lys-NH$_2$;
H-Inp-D-Bip-D-Trp-Taz-Lys-NH$_2$;
H-Inp-D-Bip-D-Trp-2Fua-Lys-NH$_2$;
H-Inp-D-Bip-D-Trp-Pff-Lys-NH$_2$;
H-Inp-D-Bip-D-Bal-2Thi-Lys-NH$_2$;
H-Inp-D-Bip-D-Bal-3Thi-Lys-NH$_2$;
H-Inp-D-Bip-D-Bal-Taz-Lys-NH$_2$;
H-Inp-D-Bip-D-Bal-2Fua-Lys-NH$_2$; or
H-Inp-D-Bip-D-Bal-Pff-Lys-NH$_2$;

or a pharmaceutically acceptable salt thereof.

4. A compound according to claim 3, wherein said compound is according to the formula:

H-Inp-D-1Nal-D-Trp-3 Pal-Lys-NH$_2$;
H-Inp-D-2Nal-D-Trp-4 Pal-Lys-NH$_2$;
H-Inp-D-2Nal-D-Trp-Orn-Lys-NH$_2$;
H-Inp-D-Bip-D-Trp-Phe-Lys-NH$_2$;
H-Inp-D-2Nal-D-Trp-Thr(Bzl)-Lys-NH$_2$;
H-Inp-D-2Nal-D-Trp-Pff-Lys-NH$_2$;
H-Inp-D-2Nal-D-Trp-2Thi-Lys-NH$_2$;
H-Inp-D-2Nal-D-Trp-Taz-Lys-NH$_2$;
H-Inp-D-Dip-D-Trp-Phe-Lys-NH$_2$;
H-Inp-D-Bpa-D-Trp-Phe-Lys-NH$_2$;
H-Inp-D-2Nal-D-Trp-3 Pal-Lys-NH$_2$;
H-Inp-D-Bal-D-Trp-Phe-Lys-NH$_2$;
H-Inp-D-Bal-D-Trp-2Thi-Lys-NH$_2$;
H-Inp-D-Bal-D-Trp-Taz-Lys-NH$_2$;
H-Inp-D-Bal-D-Trp-Taz-Apc-NH$_2$;
H-Inp-D-1Nal-D-Trp-2Thi-Lys-NH$_2$;
H-Inp-D-1Nal-D-Trp-Taz-Lys-NH$_2$;
H-Inp-D-2Nal-D-Trp-Phe-Apc-NH$_2$;
H-Inp-D-1Nal-D-Trp-Taz-Apc-NH$_2$; or
H-Inp-D-1Nal-D-Trp-Phe-Apc-NH$_2$;

or a pharmaceutically acceptable salt thereof.

5. A compound according to claim 4, wherein said compound is according to the formula:

H-Inp-D-1Nal-D-Trp-3 Pal-Lys-NH$_2$;
H-Inp-D-2Nal-D-Trp-4 Pal-Lys-NH$_2$;
H-Inp-D-Bip-D-Trp-Phe-Lys-NH$_2$;
H-Inp-D-2Nal-D-Trp-Thr(Bzl)-Lys-NH$_2$;
H-Inp-D-2Nal-D-Trp-2Thi-Lys-NH$_2$;
H-Inp-D-2Nal-D-Trp-Taz-Lys-NH$_2$;
H-Inp-D-2Nal-D-Trp-3 Pal-Lys-NH$_2$;
H-Inp-D-Bal-D-Trp-2Thi-Lys-NH$_2$;
H-Inp-D-Bal-D-Trp-Phe-Lys-NH$_2$;
H-Inp-D-1Nal-D-Trp-2Thi-Lys-NH$_2$;
H-Inp-D-2Nal-D-Trp-Phe-Apc-NH$_2$;
H-Inp-D-1Nal-D-Trp-Phe-Apc-NH$_2$;
H-Inp-D-1Nal-D-Trp-Taz-Lys-NH$_2$;
H-Inp-D-Bal-D-Trp-Taz-Lys-NH$_2$;
H-Inp-D-1Nal-D-Trp-Taz-Apc-NH$_2$; or
H-Inp-D-Bal-D-Trp-Taz-Apc-NH$_2$;

or a pharmaceutically acceptable salt thereof.

6. A compound according to claim 5, wherein said compound is according to the formula:

H-Inp-D-1Nal-D-Trp-3 Pal-Lys-NH$_2$;
H-Inp-D-2Nal-D-Trp-2Thi-Lys-NH$_2$;
H-Inp-D-2Nal-D-Trp-Taz-Lys-NH$_2$;
H-Inp-D-Bal-D-Trp-2Thi-Lys-NH$_2$;
H-Inp-D-Bal-D-Trp-Phe-Lys-NH$_2$;
H-Inp-D-1Nal-D-Trp-2Thi-Lys-NH$_2$;
H-Inp-D-2Nal-D-Trp-Phe-Apc-NH$_2$;
H-Inp-D-1Nal-D-Trp-Phe-Apc-NH$_2$;
H-Inp-D-1Nal-D-Trp-Taz-Lys-NH$_2$;
H-Inp-D-Bal-D-Trp-Taz-Lys-NH$_2$;
H-Inp-D-1Nal-D-Trp-Taz-Apc-NH$_2$; or
H-Inp-D-Bal-D-Trp-Taz-Apc-NH$_2$;

or a pharmaceutically acceptable salt thereof.

7. A compound according to claim 6, wherein said compound is according to the formula:

H-Inp-D-2Nal-D-Trp-2Thi-Lys-NH$_2$;
H-Inp-D-Bal-D-Trp-2Thi-Lys-NH$_2$;
H-Inp-D-Bal-D-Trp-Phe-Lys-NH$_2$;
H-Inp-D-1Nal-D-Trp-2Thi-Lys-NH$_2$;
H-Inp-D-1Nal-D-Trp-Phe-Apc-NH$_2$; or
H-Inp-D-Bal-D-Trp-Taz-Lys-NH$_2$;

or a pharmaceutically acceptable salt thereof.

8. A compound according to claim 7, wherein said compound is according to the formula:

H-Inp-D-2Nal-D-Trp-2Thi-Lys-NH$_2$;

or a pharmaceutically acceptable salt thereof.

9. A compound according to claim 7, wherein said compound is according to the formula:

H-Inp-D-Bal-D-Trp-Taz-Lys-NH$_2$;

or a pharmaceutically acceptable salt thereof.

10. A compound according to claim 4, wherein said compound is according to the formula:

H-Inp-D-2Nal-D-Trp-Orn-Lys-NH$_2$;

H-Inp-D-2Nal-D-Trp-Pff-Lys-NH$_2$;

H-Inp-D-Dip-D-Trp-Phe-Lys-NH$_2$; or

H-Inp-D-Bpa-D-Trp-Phe-Lys-NH$_2$;

or a pharmaceutically acceptable salt thereof.

11. A compound according to claim 10, wherein said compound is according to the formula:

H-Inp-D-2Nal-D-Trp-Pff-Lys-NH$_2$; or

H-Inp-D-Dip-D-Trp-Phe-Lys-NH$_2$;

or a pharmaceutically acceptable salt thereof.

12. A compound according to the formula:

H-Inp-D-1Nal-D-Trp-2Thi-Apc-NH$_2$; or

H-Inp-D-Bal-D-Trp-2Thi-Apc-NH$_2$;

or a pharmaceutically acceptable salt thereof.

* * * * *

UNITED STATES PATENT AND TRADEMARK OFFICE
CERTIFICATE OF CORRECTION

| | |
|---|---|
| PATENT NO. | : 8,377,865 B2 |
| APPLICATION NO. | : 12/157224 |
| DATED | : February 19, 2013 |
| INVENTOR(S) | : Zheng Xin Dong |

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 727 days.

Signed and Sealed this
Eleventh Day of November, 2014

Michelle K. Lee
*Deputy Director of the United States Patent and Trademark Office*